US010814051B2

(12) United States Patent
Shimada et al.

(10) Patent No.: US 10,814,051 B2
(45) Date of Patent: Oct. 27, 2020

(54) FILTER ELEMENT FOR BLOOD PROCESSING FILTER AND BLOOD PROCESSING FILTER

(71) Applicant: ASAHI KASEI MEDICAL CO., LTD., Tokyo (JP)

(72) Inventors: Nobukazu Shimada, Tokyo (JP); Takako Kai, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 66 days.

(21) Appl. No.: 15/736,548

(22) PCT Filed: Jun. 17, 2016

(86) PCT No.: PCT/JP2016/068171

§ 371 (c)(1),
(2) Date: Dec. 14, 2017

(87) PCT Pub. No.: WO2016/204289

PCT Pub. Date: Dec. 22, 2016

(65) Prior Publication Data

US 2018/0154053 A1 Jun. 7, 2018

(30) Foreign Application Priority Data

Jun. 17, 2015 (JP) ................................ 2015-122448
Jun. 17, 2015 (JP) ................................ 2015-122449

(51) Int. Cl.
*A61M 1/02* (2006.01)
*B01D 39/16* (2006.01)
(Continued)

(52) U.S. Cl.
CPC .............. *A61M 1/029* (2013.01); *A61M 1/02* (2013.01); *A61M 1/34* (2013.01);
(Continued)

(58) Field of Classification Search
None
See application file for complete search history.

(56) References Cited

U.S. PATENT DOCUMENTS 5,580,465 A * 12/1996 Pall .................... A61M 1/0209 210/767
2006/0173123 A1 8/2006 Yang et al.
(Continued)

FOREIGN PATENT DOCUMENTS

CN 1765981 5/2006
CN 101512057 A 8/2009
(Continued)

OTHER PUBLICATIONS

European Search Report issued in Application No. 16811763.8, dated Apr. 24, 2018.
(Continued)

*Primary Examiner* — Clare M Perrin
(74) *Attorney, Agent, or Firm* — Greenblum & Bernstein, P.L.C.

(57) ABSTRACT

The present invention provides a filter element for a blood processing filter, comprising a nonwoven fabric, wherein the quantity of crystallization heat of the uncrystallized portion of the nonwoven fabric is 5 J/g or smaller before steam heat treatment.

19 Claims, 1 Drawing Sheet

(51) Int. Cl.
*A61M 1/34* (2006.01)
*B01D 29/00* (2006.01)

(52) U.S. Cl.
CPC ..... *B01D 29/0004* (2013.01); *B01D 39/1623* (2013.01); *A61M 2202/0057* (2013.01); *A61M 2202/0071* (2013.01); *A61M 2202/0439* (2013.01); *B01D 2239/0478* (2013.01)

(56) References Cited

U.S. PATENT DOCUMENTS

| | | | | |
|---|---|---|---|---|
| 2006/0184085 | A1 | 8/2006 | Kimura et al. | |
| 2006/0207937 | A1* | 9/2006 | Bonaguidi .......... | A61M 1/3633 210/645 |
| 2009/0234266 | A1* | 9/2009 | Solomon ............. | A61M 1/1678 604/6.09 |
| 2009/0253329 | A1 | 10/2009 | Toshiyuki et al. | |

FOREIGN PATENT DOCUMENTS

| | | |
|---|---|---|
| CN | 202554574 U | 11/2012 |
| EP | 2450431 | 5/2012 |
| JP | 60-193468 | 10/1985 |
| JP | 63-175157 | 7/1988 |
| JP | 4134043 | 5/1992 |
| JP | 08-006239 | 1/1996 |
| JP | 2565762 | 10/1996 |
| JP | 4565762 | 10/1996 |
| JP | 2001-112862 | 4/2001 |
| JP | 2006-518420 | 8/2006 |
| JP | 2008-528789 | 7/2008 |

OTHER PUBLICATIONS

International Search Report from Patent Application No. PCT/JP2016/068171, dated Sep. 6, 2016.

* cited by examiner

FILTER ELEMENT FOR BLOOD PROCESSING FILTER AND BLOOD PROCESSING FILTER

TECHNICAL FIELD

The present invention relates to a filter for a blood processing filter that is used for removing unnecessary components from blood, i.e., whole blood and blood products (liquids obtained by preparation from whole blood, and these liquids supplemented with various additives), a filter element therefor. In particular, the present invention relates to a blood processing filter suitable for leukocyte removal from the leukocyte-containing liquids as described above, and a filter element therefor.

BACKGROUND ART

In the field of blood transfusion, so-called blood component transfusion of separating a blood component necessary for a recipient from a whole blood product and transfusing the blood component has generally been practiced in addition to so-called whole blood transfusion of transfusing a whole blood product in which blood collected from a donor is supplemented with an anticoagulant. The blood component transfusion includes red cell transfusion, platelet transfusion, plasma transfusion, and the like depending on the type of the blood component necessary for a recipient, and the blood product used for these transfusions includes a red cell product, a platelet product, a plasma product, and the like.

Furthermore, so-called leukocyte-free blood transfusion of transfusing a blood product after removing leukocytes contained in the blood product has become widespread recently. This is because it has been revealed that relatively slight adverse reactions accompanying blood transfusion, such as headache, nausea, chill, or febrile non-hemolytic reaction, and severe adverse reactions having serious effects on a recipient, such as alloantigen sensitization, viral infection, or post-transfusion GVHD, are mainly caused by leukocytes contained in the blood product used in blood transfusion. For preventing relatively slight adverse reactions such as headache, nausea, chill, or fever, it is considered necessary to remove leukocytes in the blood product until the residual rate becomes from $10^{-1}$ to $10^{-2}$ or less. Also, for preventing alloantigen sensitization or viral infection, which is a severe adverse reaction, it is considered necessary to remove leukocytes until the residual rate becomes from $10^{-4}$ to $10^{-6}$ or less.

Furthermore, in recent years, leukocyte removal therapy by the extracorporeal circulation of blood has been practiced in the treatment of diseases such as rheumatism or ulcerative colitis, and high clinical effects have been obtained.

Currently, methods of removing leukocytes from the blood product are roughly classified into two types: a centrifugation method of separating and removing leukocytes by using a centrifuge and utilizing the difference in specific gravity among blood components, and a filter method of removing leukocytes by using a filter material consisting of a fiber assembly such as a nonwoven fabric or a porous structure having continuous pores, or the like. The filter method which removes leukocytes by adhesion or adsorption is most widely used at present because of having the advantages that the operation is simple and the cost is low, for example.

In recent years, new demands for leukocyte removal filters have been proposed in the medical practice. One of the demands is to improve the recovery rate of useful components used as the blood product, such as plasma proteins. Although blood, which is a raw material for the blood product, is valuable blood that is covered by blood donation with good intentions in most cases, there is a problem that plasma proteins and red cell products that have been adsorbed on a filter material in a leukocyte removal filter and thus become impossible to recover are disposed of together with the filter and end up in the garbage. Therefore, it is of significant importance to reduce the amount of the useful components adsorbed as compared with the current leukocyte removal filter and improve the recovery rate.

Thus, a leukocyte removal filter apparatus packed with a smaller amount of a filter material than ever by using a leukocyte removal filter material whose leukocyte removal performance per unit volume is high has been desired for satisfying the aforementioned demands in the medical practice. It is expected that the amount of blood remaining in the filter is decreased with decrease in the packing amount of the filter material so that the recovery rate of useful components can be improved over the conventional filter apparatus.

In the market, there has been a further demand for the leukocyte removal filter to process a desired amount of blood in a short time. Therefore, the leukocyte removal filter apparatus may need to have a shape in which the cross section is equal to or larger than that of the conventional apparatus and the thickness of the filter material is thinner. However, for decreasing the thickness of the filter material while maintaining the leukocyte removal performance, it is necessary to enhance the leukocyte removal performance per unit volume.

The mechanism of leukocyte removal with a filter material such as a fiber assembly or a porous structure having continuous pores is considered to be based mainly on the adhesion or adsorption of leukocytes contacted with the filter material surface onto the filter material surface. Accordingly, in order to satisfy the aforementioned demands, studies to decrease the fiber diameter of the nonwoven fabric or increase the bulk density, for example, have been conducted as an approach for improvement in the leukocyte removal performance of the conventional filter material (see Patent Literature 1 and 2).

Furthermore, a leukocyte removal method that attains high leukocyte removal performance and has a short processing time without causing clogging by using a leukocyte removal filter in which a specific structure in the thickness direction, i.e., the flow direction of liquids, is rendered uniform over the entire filtration surface of the nonwoven fabric has been proposed as another approach (see Patent Literature 3).

CITATION LIST

Patent Literature

Patent Literature 1: Japanese Patent Laid-Open No. 60-193468
Patent Literature 2: U.S. Pat. No. 5,580,465
Patent Literature 3: Japanese Patent No. 4134043

SUMMARY OF INVENTION

Technical Problem

However, it has been revealed that leukocyte removal performance is not improved in many cases even when the physical properties of filter elements are optimized according to the description of Patent Literature 1 to 3.

The present inventor has studied the cause and consequently found that, although leukocyte removal filters with the filter elements incorporated therein are subjected to steam heat treatment for the purpose of, for example, sterilizing the leukocyte removal filters, this steam heat treatment drastically reduces the leukocyte removal performance of the filters as compared with that before the sterilization.

Blood processing filters, particularly, leukocyte removal filters, are usually subjected to sterilization treatment such as steam heat treatment before use in order to prevent the contamination of blood products with infectious substances. It has been revealed that the properties of the filter elements in the inside of the filters are changed in association with the treatment, resulting in reduction in leukocyte removal performance.

In light of the problems of the conventional techniques, an object of the present invention is to provide a filter element for a blood processing filter having leukocyte removal performance equal to or better than that of conventional filter elements even after steam heat treatment, and a blood processing filter.

Solution to Problem

The present inventor has conducted diligent studies to attain high removal performance for leukocytes and the like even after steam heat treatment by a blood processing filter having a filter element containing a nonwoven fabric, held by a container, and consequently found that the removal performance for leukocytes and the like of conventional filter elements after steam heat treatment can be drastically improved by adjusting the crystallinity of the nonwoven fabric before the steam heat treatment to a predetermined level or larger.

Specifically, the present invention is as follows:

[1] A filter element for a blood processing filter, comprising a nonwoven fabric, wherein the quantity of crystallization heat of the uncrystallized portion of the nonwoven fabric is 5 J/g or smaller before steam heat treatment.

[2] The filter element for a blood processing filter according to [1], wherein a value obtained by subtracting the quantity of crystallization heat of the uncrystallized portion of the nonwoven fabric from its quantity of heat of crystal melting is 50 J/g or larger before steam heat treatment.

[3] The filter element for a blood processing filter according to [1] or [2], wherein the X-ray crystallinity of the nonwoven fabric is 60 or larger before steam heat treatment.

[4] The filter element according to any of [1] to [3], wherein the area contraction rate of the nonwoven fabric is 10% or smaller.

[5] The filter element according to any of [1] to [4], wherein the nonwoven fabric has a nonionic group and a basic nitrogen-containing functional group in the surface portion thereof.

[6] The filter element for a blood processing filter according to any of [1] to [5], wherein the heat shrinkage rate of the nonwoven fabric is from 5 to 24%, and the elongation rates of the nonwoven fabric both in a direction where the elongation rate is maximized and in a direction vertical thereto are 1% or more and 3% or less.

[7] The filter element for a blood processing filter according to [6], wherein the difference between the elongation rate of the nonwoven fabric in the direction where the elongation rate is maximized and its elongation rate in the direction vertical thereto is 1% or less.

[8] A blood processing filter comprising a filter element according to any of [1] to [7], an inlet-side container member, and an outlet-side container member, wherein the inlet-side container member and the outlet-side container member are each made of a rigid material, the filter element is held such that the outer edges of the filter element are bound by the inlet-side container member and the outlet-side container member, and the internal space of the blood processing filter is partitioned by the filter element into inlet space and outlet space.

[9] A blood processing filter having a filter element according to any of [1] to [7] and a container having an inlet and an outlet, wherein the container is made of a soft material, the filter element is welded to the periphery of the container, and the internal space of the blood processing filter is partitioned by the filter element into inlet space and outlet space.

[10] The blood processing filter according to [8] or [9], wherein the filter element comprises a plurality of nonwoven fabrics, and the quantity of crystallization heat of the uncrystallized portion of a nonwoven fabric contacted with the inlet-side container member and/or a nonwoven fabric contacted with the outlet-side container member among the plurality of nonwoven fabrics is 5 J/g or smaller before steam heat treatment.

[11] The blood processing filter according to any of [8] to [10], wherein the packing density of the filter element is 0.1 $g/cm^3$ or higher and 0.5 $g/cm^3$ or lower.

Advantageous Effects of Invention

Use of the filter element of the present invention enables a blood processing filter to be provided which can maintain its high removal performance for leukocytes and the like even after steam heat treatment.

DESCRIPTION OF EMBODIMENTS

Figure 1:
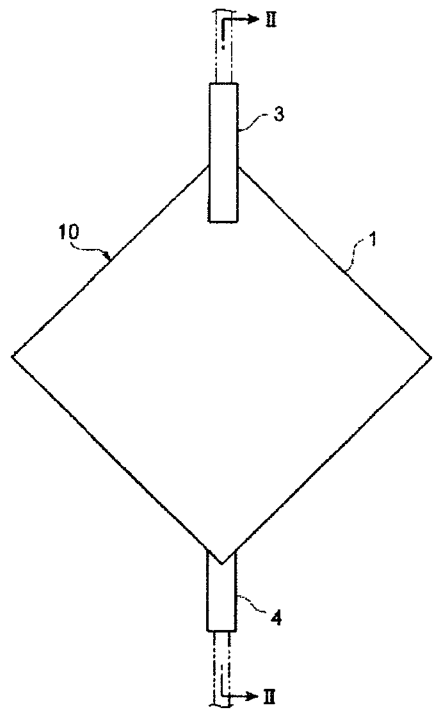
FIG. 1 is a schematic view of a blood processing filter equipped with a filter element for a blood processing filter according to one embodiment of the present invention.

Hereinafter, a mode for carrying out the present invention (hereinafter, referred to as the present embodiment) will be described in detail. However, the present invention is not limited to the embodiment given below, and various changes or modifications can be made therein without departing from the spirit of the present invention.

In the present embodiment, the filter element comprises a nonwoven fabric.

Specifically, the filter element may comprise one nonwoven fabric or may comprise a plurality of nonwoven fabrics. Alternatively, the filter element may comprise the nonwoven fabric in combination with an additional sheet.

When the filter element comprises a plurality of nonwoven fabrics, the plurality of nonwoven fabrics may be of single type or may be of plural types.

In the filter element of the present embodiment, the nonwoven fabric may be a raw (original) fabric that is just reeled out from a fabric roll, may be provided with, for example, a surface layer such as a coat layer, or may be subjected to a surface treatment process such as a heat process or electron beam irradiation. When the nonwoven fabric is provided with a surface layer by coating treatment, examples of the coating agent used include, but are not limited to, hydrophilic polymers. The coating agent can be any hydrophilic polymer that swells in water but is not dissolved in water.

In the present embodiment, the nonwoven fabric is not particularly limited and includes, for example, resin fibers formed by spinning a resin that does not influence blood, such as polyamide, polyester (polyethylene terephthalate (PET), polybutylene terephthalate (PBT), etc.), polyacrylonitrile, polyurethane, polyvinyl formal, polyvinyl acetal, polytrifluorochloroethylene, poly(meth)acrylate, polysulfone, polystyrene, polyethylene, polypropylene, cellulose, or cellulose acetate, by a melt blown method or the like.

In the present embodiment, the quantity of crystallization heat of the uncrystallized portion of the nonwoven fabric contained in the filter element is 5 J/g or smaller before steam heat treatment.

In this context, the steam heat treatment refers to exposure to steam at a temperature of 100° C. or higher.

A blood processing filter comprising the filter element of the present embodiment includes a blood processing filter in which a container having an inlet for introducing a liquid to be processed (e.g., blood or a blood product) to the inside of the container, and an outlet for discharging this liquid to the outside of the container is packed with the filter element. In such a filter, the internal space of the filter is partitioned by the filter element into inlet space and outlet space.

For example, the blood processing filter can be configured to comprise a filter element and an inlet-side container member and an outlet-side container member disposed to sandwich the filter element, wherein the inlet-side container member and the outlet-side container member have holding parts for holding the filter element by bonding its outer edges, can be configured such that the filter element is sandwiched or wrapped by a soft member (container) made of a soft material such as a flexible synthetic resin sheet having an inlet and an outlet, and is welded to the periphery of the soft member, or can be configured such that the outer edges of the filter element are bonded with a soft member, and the soft member of the bonded portion is bonded with another soft member or the like having an inlet and an outlet.

The blood processing filter may contain a member other than the filter element of the present embodiment, in the inside of the container. For example, a pre-filter for capturing microaggregates may be disposed on an upstream side (side closer to the container inlet than the filter element of the present embodiment) in the inside of the container, or a post-filter may be disposed on a downstream side (side closer to the outlet than the filter element) in the inside of the container.

Figure 2:
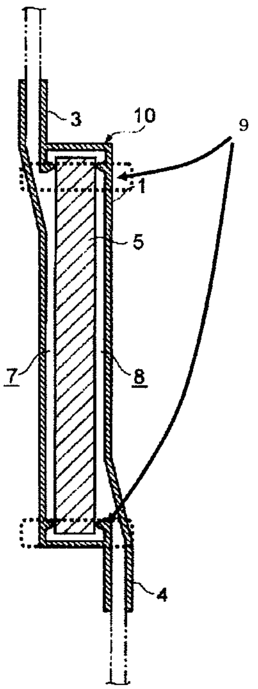
FIG. 2 is a cross-sectional view of a blood processing filter equipped with a filter element for a blood processing filter according to one embodiment of the present invention.

FIG. 1 is a schematic view of a blood processing filter (leukocyte removal filter) equipped with the filter element of the present embodiment, and FIG. 2 is a cross-sectional view taken along the II-II line of FIG. 1.

As shown in FIGS. 1 and 2, a blood processing filter 10 has a flat container 1 and a blood processing filter element 5 in a substantially dry state housed in the inside thereof. The container 1 which houses the blood processing filter element 5 comprises two elements: an inlet-side container member having a first port 3 at the end part of one principal surface; and an outlet-side container material having a second port 4 at the end part of the other principal surface. The space within the flat container 1 is partitioned by the blood processing filter element 5 into space 7 on the first port side and space 8 on the second port side.

This blood processing filter 1 assumes a structure where the inlet-side container member and the outlet-side container member are disposed to sandwich the filter element 5, and these two container members hold the filter element 5 such that holding parts (rib-shaped convex parts, etc.), which are provided on a portion on the internal side of the peripheries of respective members, bind outer edges 9 of the filter element 5. These convex parts squeeze together to bind the filter element so that blood flows into the filter element within the internal side of the convex parts in order for the blood to be filtered. The filter element can be compressed at a high density by the convex parts to thereby prevent side flow in which blood escapes over the outer edges of the filter element and passes without being filtered.

The blood processing filter 1 is usually subjected to sterilization treatment by a steam heat treatment method before use. In this respect, the physical structure of the nonwoven fabric is thought to be largely changed by the steam heat treatment. Particularly, if the nonwoven fabric contracts in the planar direction, the holding parts mentioned above consequently become structurally unstable to thereby reduce the removal performance for leukocytes and the like of the blood processing filter 1 and handleability.

Examples of the change in the physical properties of the nonwoven fabric in association with the steam heat treatment include contraction in the planar direction as well as change in the shape of the fibers constituting the nonwoven fabric. As a result, the surface area per unit mass (specific surface area) of the filter element is decreased, and removal performance for leukocytes and the like may be reduced. Also, the mean flow pore size in the vertical direction (thickness direction) of the filter element is increased. As a result, the airflow pressure drop of the filter element per unit weight is reduced, probably leading to reduction in removal performance for leukocytes and the like. As mentioned above, the change in the physical properties of the nonwoven fabric in association with the steam heat treatment is a reason for largely deteriorating the structure or the performance balance of the blood processing filter.

The present inventor has studied the cause of the change in the physical properties of the nonwoven fabric in association with the steam heat treatment and consequently found that part of the reason is insufficient crystallinity of the resin (polyethylene terephthalate resin, etc.) to form the nonwoven fabric. In short, it is considered that a low crystalline resin is heat-treated at a high temperature (particularly, a high temperature equal to or higher than its glass transition temperature (Tg)) so that the resin density in the nonwoven fabric is elevated due to the increased crystallization of the nonwoven fabric to thereby decrease the volume per unit weight of the nonwoven fabric, accordingly causing change in physical properties, such as contraction or change in fiber shape, and thereby destabilizing the structure of the blood processing filter or losing performance balance.

In the present embodiment, the quantity of crystallization heat of the uncrystallized portion of the nonwoven fabric contained in the filter element is set to 5 J/g or smaller before steam heat treatment. The "quantity of crystallization heat of the uncrystallized portion" is an index that indicates the crystallinity of a resin. A smaller value of this "quantity of crystallization heat of the uncrystallized portion" means higher crystallinity of the resin. The quantity of crystallization heat of the uncrystallized portion is preferably 3 J/g or smaller, more preferably 2 J/g or smaller, further preferably 1 J/g or smaller.

This can suppress change in the physical properties of the nonwoven fabric in association with steam heat treatment or the like and maintain high removal performance for leukocytes and the like. In general, conditions for the steam heat treatment differ variously depending on kits incorporating the blood processing filter produced by each bag manufacturer. The filter element of the present embodiment has thermally stable nature and therefore has heat stability that allows the blood processing filter to withstand a wider range of steam heat treatment conditions as compared with blood processing filters using conventional filter elements.

Use of the filter element comprising such a nonwoven fabric is also effective for improving performance and handleability as a blood processing filter.

For example, in the filter in which the filter element is sandwiched and held by the rigid container as shown in FIGS. 1 and 2, the rebound strength of the filter element against the holding parts of the container is high even after steam heat treatment so that the strong holding state of the filter element by the container holding parts is maintained. This can suppress a phenomenon in which blood leaks through the gaps between the holding parts and the filter element and runs into the outlet space from the inlet space without passing through the filter element (side leak phenomenon). Thus, the effect of improving removal performance for leukocytes and the like is obtained.

Furthermore, in a filter in which the filter element is sandwiched by a soft (flexible) container and bonded to the container by high-frequency welding, the strength of the bonded part between the container and the filter element can be improved by controlling the quantity of crystallization heat of the uncrystallized portion of the nonwoven fabric to a predetermined level or smaller. Thus, the effect of improving the resistance to centrifugation (crack resistance of the bonded part between the container and the filter element when the filter is centrifuged (when centrifugal force is applied to the filter) of the filter is also obtained. Although it is uncertain why the strength of the bonded part by high-frequency welding between the container and the filter element is improved by controlling the quantity of crystallization heat of the uncrystallized portion of the nonwoven fabric contained in the filter element to a predetermined level or smaller, it is considered that the increased crystallinity of the nonwoven fabric elevates the rebound force of the nonwoven fabric during high-frequency welding to thereby suppress excessive melting caused by the pressure bonding of the nonwoven fabric so that a homogeneous bonded part (free of sinkholes or the like generated by excessive melting) can be formed.

The value obtained by subtracting the quantity of crystallization heat of the uncrystallized portion of the nonwoven fabric contained in the filter element from its quantity of heat of crystal melting is preferably 50 J/g or larger before steam heat treatment. This "value obtained by subtracting the quantity of crystallization heat of the uncrystallized portion from the quantity of heat of crystal melting" is also an index that indicates the crystallinity of a resin. A larger value thereof means higher crystallinity of the resin. The further increased crystallinity of the filter element further suppresses change in the physical properties (contraction, etc.) of the filter element between before and after steam heat treatment. In this way, the effect of enhancing removal performance for leukocytes and the like is obtained, as mentioned above.

The value obtained by subtracting the quantity of crystallization heat of the uncrystallized portion from the quantity of heat of crystal melting is more preferably 55 J/g or larger, further preferably 60 J/g or larger, most preferably 65 J/g or larger.

In the present embodiment, the quantity of crystallization heat of the uncrystallized portion and the quantity of heat of crystal melting are values measured as to the nonwoven fabric by differential scanning calorimetry (DSC). Such a measurement method will be described below.

From 3 to 4 mg of the nonwoven fabric is separated and loaded in an aluminum standard container. An initial heating curve (DSC curve) is measured at an initial temperature of 35° C. at a heating rate of 10° C./min in an atmosphere of 50 mL/min nitrogen flow. An exothermic peak and a melting peak (endothermic peak) are detected from this initial heating curve (DSC curve). The values of quantity of heat (J) obtained from their respective peak areas are divided by the mass of the nonwoven fabric to calculate the quantity of crystallization heat of the uncrystallized portion (J/g) and the quantity of heat of crystal melting (J/g).

For example, TA-60WS system manufactured by Shimadzu Corp. can be used as a measurement apparatus.

In the present embodiment, the X-ray crystallinity of the nonwoven fabric contained in the filter element is preferably 60 or larger before steam heat treatment. The further increased crystallinity of the filter element suppresses change in the physical properties (contraction, etc.) of the filter material between before and after steam heat treatment. In this way, the effect of enhancing removal performance for leukocytes and the like is obtained, as mentioned above.

The X-ray crystallinity is more preferably 63 or larger, further preferably 66 or larger.

In the present embodiment, the X-ray crystallinity is measured by an X-ray diffraction method.

The measurement can be performed by the following measurement steps 1) to 5) using an X-ray diffraction apparatus (e.g., MiniFlexll (Rigaku Corp., model 2005H301)):

1) One nonwoven fabric having a size of 3 cm×3 cm is loaded on a sample table.

2) The sample is assayed under the following conditions:

Scanning range: from 5° to 50°
Sampling width (width for data fetch): 0.02°
Scan speed: 2.0°/min
Voltage: 30 kV
Current: 15 mA 3) After the assay, data with peaks from an amorphous part and a crystalline part being separated from each other is obtained.

4) An amorphous peak area (Aa) and a total peak area (At) are determined from the data of the step 3). The data obtained in the step 3) is analyzed with, for example, analytical software (MDI JADE 7) to carry out an "automatic peak separation" function. As a result, the amorphous peak area (Aa) and the total peak area (At) are automatically calculated.

5) The crystallinity is calculated according to the following expression from the amorphous peak area (Aa) and the total peak area (At):

$$\text{Crystallinity}(\%)=(At-Aa)/At\times 100$$

The nonwoven fabric whose quantity of crystallization heat of the uncrystallized portion is 5 J/g or smaller, the nonwoven fabric whose value obtained by subtracting the quantity of crystallization heat of the uncrystallized portion from the quantity of heat of crystal melting is 50 J/g or larger, and the nonwoven fabric having X-ray crystallinity of 60 or larger, before steam heat treatment can be easily produced, for example, by selecting a material or production conditions therefor as described in the present specification.

In the present embodiment, the area contraction rate of the nonwoven fabric is preferably 10% or smaller, more preferably 3% or smaller, particularly preferably 2% or smaller, most preferably 1% or smaller. If the area contraction rate is larger than 10%, there is a tendency that, when severe steam heat treatment such as high-pressure steam sterilization is conducted, not only is the pore size of the nonwoven fabric decreased but the pore size becomes non-uniform to thereby increase clogging by blood cells and decrease processing speed. On the other hand, the area contraction rate of 10% or smaller is preferred because there is a tendency that the pore size is kept uniform even after sterilization treatment so that variation in processing speed can be prevented, and stable performance balance can be exerted.

In this respect, for example, polybutylene terephthalate has a faster crystallization speed than that of other polyester fibers, for example, polyethylene terephthalate fibers. Therefore, its crystallinity is easily elevated. The resulting nonwoven fabric is less likely to contract in the planar direction even by severe steam heat treatment such as high-pressure steam sterilization (the area contraction rate is easily reduced) and can thus exert stable removal performance for leukocytes and the like and processing speed, irrespective of sterilization conditions.

The area contraction rate of the nonwoven fabric according to the present embodiment is calculated according to the following expression by accurately measuring the horizontal and vertical sizes of the nonwoven fabric before steam heat treatment cut into a square of approximately 20 cm×20 cm, then performing steam heat treatment at 115° C. for 240 minutes without fixing the nonwoven fabric with a pin or the like, and then measuring the horizontal and vertical sizes again:

Area contraction rate (%)=(Vertical length (cm) of the nonwoven fabric before the heat treatment×Horizontal length (cm) of the nonwoven fabric before the heat treatment−Vertical length (cm) of the nonwoven fabric after the heat treatment×Horizontal length (cm) of the nonwoven fabric after the heat treatment)/(Vertical length (cm) of the nonwoven fabric before the heat treatment×Horizontal length (cm) of the nonwoven fabric before the heat treatment)×100

The nonwoven fabric contained in the filter element may further comprise a nonwoven fabric having a nonionic hydrophilic group and a basic nitrogen-containing functional group in a surface portion. For example, the fiber itself constituting the nonwoven fabric may have the nonionic hydrophilic group and the basic nitrogen-containing functional group in its surface portion, or a coat layer formed on the nonwoven fabric may have the nonionic hydrophilic group and the basic nitrogen-containing functional group in its surface portion.

The surface portion of the nonwoven fabric refers to the surface portion of the coat layer when the surface of the nonwoven fabric is coated with a coat layer containing a monomer and/or a polymer, etc., and refers to the surface portion of spun fibers when no coat layer is formed on the fibers.

The filter element having a nonionic hydrophilic group and a basic nitrogen-containing functional group in a surface portion can enhance the affinity of the nonwoven fabric for leukocytes in blood while enhancing the blood product permeability of the nonwoven fabric. Thus, leukocyte removal can be efficiently performed.

When the filter element comprises two or more nonwoven fabrics (mentioned later), at least one of the nonwoven fabrics can have the nonionic hydrophilic group and the basic nitrogen-containing functional group in the surface portion.

The ratio of the basic nitrogen-containing functional group to the total of the nonionic hydrophilic group and the basic nitrogen-containing functional group in the surface portion is preferably from 0.2 to 4.0% by mass, more preferably from 0.3 to 1.5% by mass. The ratio of the basic nitrogen-containing functional group can be measured by analysis based on NMR, IR, TOF-SIMS, or the like. The ratio between the basic nitrogen-containing functional group and the nonionic hydrophilic group can be set as described above to thereby secure stable wettability for blood and also efficiently remove leukocytes and the like while suppressing the unnecessary clogging of blood components such as platelets.

Examples of the nonionic hydrophilic group include alkyl groups, alkoxy group, carbonyl groups, aldehyde groups, phenyl groups, amide groups, and hydroxyl groups. Examples of the basic nitrogen-containing functional group include amino groups represented by $—NH_2$, $—NHR_1$, $—NR_2R_3$, or $—N^+R^4R^5R^6$ ($R^1$, $R^2$, $R^3$, $R^4$, $R^5$, and $R^6$ each represent an alkyl group having from 1 to 3 carbon atoms).

The coat layer can contain, for example, a copolymer having a monomer unit having the nonionic hydrophilic group and a monomer unit having the basic nitrogen-containing functional group. Examples of the monomer unit having the nonionic hydrophilic group include units derived from 2-hydroxyethyl (meth)acrylate, 2-hydroxypropyl (meth)acrylate, vinyl alcohol, (meth)acrylamide, N-vinylpyrrolidone, and the like. Among these monomers, 2-hydroxyethyl (meth)acrylate is preferably used in view of easy availability, easy handling during polymerization, performance when blood flows, etc. The monomer unit of vinyl alcohol is usually formed by hydrolysis after polymerization of vinyl acetate.

Examples of the monomer unit having the basic nitrogen-containing functional group include units derived from: derivatives of (meth)acrylic acid such as diethylaminoethyl (meth)acrylate, dimethylaminoethyl (meth)acrylate, dimethylaminopropyl (meth)acrylate, and 3-dimethylamino-2-hydroxypropyl (meth)acrylate; styrene derivatives such as p-dimethylaminomethylstyrene and p-diethylaminoethylstyrene; vinyl derivatives of nitrogen-containing aromatic compounds such as 2-vinylpyridine, 4-vinylpyridine, and 4-vinylimidazole; derivatives in which the vinyl compounds described above are converted to quaternary ammonium salts with alkyl halides or the like; and the like. Among these monomers, diethylaminoethyl (meth)acrylate and dimethylaminoethyl (meth)acrylate are preferably used in view of easy availability, easy handling during polymerization, performance when blood flows, etc.

The mass of the coat layer is, for example, from approximately 1.0 to 40.0 mg with respect to 1 g in total of the masses of the nonwoven fabric and the coat layer.

The mass of the coat layer can be calculated by, for example, the following procedures: the nonwoven fabric before carrying the coat layer is dried for 1 hour in a dryer set to 60° C., and then left for 1 hour or longer in a desiccator, followed by the measurement of the mass (A g). The nonwoven fabric having the coat layer is similarly dried for 1 hour in a dryer of 60° C. and then left for 1 hour or longer in a desiccator, followed by the measurement of the mass (B g). The mass of the coat layer is calculated according to the following expression:

Mass (mg/g) of the coat layer with respect to 1 g in total of the nonwoven fabric and the coat layer$=(B-A)\times 1000/B$.

The coat layer containing the polymer (copolymer) can be formed by, for example, a method which involves dipping the nonwoven fabric in a polymer solution containing the polymer and a solvent, and then removing the solvent from the polymer solution attached to the nonwoven fabric.

In the case of preparing a filter by sandwiching and holding a filter element by two parts, outlet-side and inlet-side container members, constituting a rigid container (e.g., as shown in FIGS. 1 and 2), when the filter element comprises a plurality of nonwoven fabrics, a nonwoven fabric having high crystallinity is used as a nonwoven fabric contacted with the outlet-side container member (nonwoven fabric disposed at the nearest position to the outlet-side container member) so that the filter element can be more strongly bound by the holding part of the outlet-side container member after steam heat treatment. This suppresses a phenomenon in which blood leaks through the gaps between the holding parts and the filter element and directly runs into the outlet space from the inlet space without passing through the filter element (side leak phenomenon). Thus, the effect of improving removal performance for leukocytes and the like is obtained, and performance as a blood processing filter can be further improved.

Specifically, in the case of preparing a filter by sandwiching and holding a filter element by two parts, outlet-side and inlet-side container members, constituting a rigid container, a nonwoven fabric contacted with the outlet-side container member among the nonwoven fabrics contained in the filter element preferably possesses the following (1) and more preferably possesses (2) and/or (3) in addition to (1):

(1) the quantity of crystallization heat of the uncrystallized portion is 5 J/g or smaller before steam heat treatment, (2) the value obtained by subtracting the quantity of crystallization heat of the uncrystallized portion from the quantity of heat of crystal melting is 50 J/g or larger before steam heat treatment, and (3) the X-ray crystallinity is 60 or larger before steam heat treatment.

In the case of preparing a filter by sandwiching and holding a filter element by two parts, outlet-side and inlet-side container members, constituting a rigid container, the filter is excellent in terms of removal performance for leukocytes and the like after steam heat treatment if all of the nonwoven fabrics contained in the filter element have high crystallinity. However, the filter is inferior in terms of the ease of sandwiching and holding the filter element by the container members or bonding the filter element with the container members, due to the increased rebound strength of the filter element. Therefore, from the viewpoint of productivity in filter production, it is rather preferred that among the nonwoven fabrics contained in the filter element, a nonwoven fabric other than the nonwoven fabric contacted with the inlet-side container member or the outlet-side container member (or the nonwoven fabric contacted with the inlet-side container member or the outlet container member and a predetermined number (usually, from one to several) of nonwoven fabrics disposed adjacently thereto) should not have too high crystallinity.

When the filter element held in a rigid container comprises, for example, first and second nonwoven fabric layers (mentioned later) in this order from the inlet side, it is preferred that among a plurality of nonwoven fabrics contained in the second nonwoven fabric layer, a nonwoven fabric contacted with the outlet-side container member (and a predetermined number of nonwoven fabrics disposed adjacently thereto) should satisfy at least (1) described above, and one or some or all of the other nonwoven fabrics should not satisfy (1) described above or, if satisfying (1), should have a larger quantity of crystallization heat of the uncrystallized portion before steam heat treatment than that of the nonwoven fabric contacted with the outlet-side container member, from the viewpoint of productivity in filter production.

The nonwoven fabric contained in the filter element 5 of the present embodiment preferably has a formation index of 15 or larger and 70 or smaller corresponding to a thickness of 0.3 mm. If the formation index is larger than 70, the structure in the thickness direction of the nonwoven fabric is non-uniform relative to the filtration surface direction so that blood does not flow evenly in the nonwoven fabric. Therefore, removal performance for leukocytes and the like tends to be reduced. On the other hand, if the formation index is smaller than 15, clogging is more likely to occur due to a rise in liquid-flow resistance so that processing speed is slowed down. The formation index is more preferably 15 or larger and 65 or smaller, further preferably 15 or larger and 60 or smaller, particularly preferably 15 or larger and 50 or smaller, most preferably 15 or larger and 40 or smaller.

The formation index in the present embodiment is a value obtained by irradiating the nonwoven fabric with light from underneath, detecting the transmitted light with a charge-coupled device camera (hereinafter, abbreviated to a "CCD camera"), and multiplying the coefficient of variation (%) of the absorbance of the porous body (nonwoven fabric) detected by each pixel of the CCD camera by ten.

In the present embodiment, the formation index can be measured with, for example, a formation tester FMT-MIII (Nomura Shoji Co., Ltd.; manufactured in 2002; S/N: 130). The basic setting of the tester is not changed after shipment from the factory, and the measurement can be carried out such that the total number of pixels of a CCD camera is, for example, approximately 3400. Specifically, the measurement can be performed by adjusting the measurement size to 7 cm×3 cm (one pixel size=0.78 mm×0.78 mm) such that the total number of pixels is approximately 3400. Alternatively, the measurement size may be changed according to the shape of a sample such that the total number of pixels is equal to 3400.

The formation index depends largely on the thickness of the nonwoven fabric. Therefore, the formation index corresponding to a thickness of 0.3 mm is calculated by the following method.

First, 3 nonwoven fabrics having a thickness of 0.3 mm or smaller are provided, and their respective formation indexes and thicknesses are measured. The thicknesses at arbitrary four points are measured at a measurement pressure of 0.4 N using a constant-pressure thickness meter (e.g., Ozaki Mfg. Co., Ltd., model FFA-12), and an average value thereof is used as the thickness of the nonwoven fabric. Next, two out of the 3 nonwoven fabrics thus assayed are stacked such that the thickness is 0.3 mm or larger. The formation index and the thickness of the two nonwoven fabrics in a stacked state are measured. After the completion of formation index measurement as to a total of 3 combinations, a linear regression equation of the thickness and the formation index is determined. The formation index corresponding to a thickness of 0.3 mm is determined from the equation.

The thickness of two nonwoven fabrics may fall short of 0.3 mm. In this case, a plurality of nonwoven fabrics are prepared and stacked such that the thickness of the stacked nonwoven fabrics is 0.3 mm or larger, followed by formation index measurement. Next, the number of the stacked nonwoven fabrics is reduced such that the thickness of the stacked nonwoven fabrics becomes 0.3 mm or smaller, and the formation index is measured. The formation index is measured for all combinations of the nonwoven fabrics in which the thickness of the stacked nonwoven fabrics is 0.3 mm or smaller. A linear regression equation of the thickness and the formation index is determined. The formation index corresponding to a thickness of 0.3 mm can be determined from the equation.

The 3 or more nonwoven fabrics used in the formation index measurement are preferably cut out from a single filter element. They are usually nonwoven fabrics having substantially the same quality, i.e., nonwoven fabrics having the same physical properties (material, fiber diameter, bulk density, etc.). However, if the required number of nonwoven fabrics having substantially the same quality for the measurement cannot be obtained from a single filter element, the measurement can be performed by using nonwoven fabrics from filter elements of the same type in combination therewith.

The specific method for calculating the formation index is also described in the paragraphs [0016] to [0018] of Patent Literature 3.

The specific surface area of the nonwoven fabric contained in the filter element 5 of the present embodiment is preferably 0.8 $m^2/g$ or larger and 5.0 $m^2/g$ or smaller. If the specific surface area is larger than 5.0 $m^2/g$, there is a tendency that useful components such as plasma proteins are adsorbed onto the filter element during blood processing so that the recovery rate of the useful components is reduced. Furthermore, a blood filtration rate may be extremely reduced, or the filter element may not be stably produced. If the specific surface area is smaller than 0.8 $m^2/g$, there is a tendency that removal performance for leukocytes and the like is reduced as compared with conventional filter elements because the amount of leukocytes adsorbed is decreased due to the reduced frequency of contact between leukocytes and the filter element.

The specific surface area of the nonwoven fabric is more preferably 1.0 $m^2/g$ or larger and 3.2 $m^2/g$ or smaller, further preferably 1.1 $m^2/g$ or larger and 2.9 $m^2/g$ or smaller, particularly preferably 1.2 $m^2/g$ or larger and 2.9 $m^2/g$ or smaller, most preferably 1.2 $m^2/g$ or larger and 2.6 $m^2/g$ or smaller.

In the blood processing filter, a plurality of filter elements with different specific surface areas may be disposed so that the specific surface areas increase as they approach the outlet side.

The specific surface area according to the present embodiment refers to the surface area of the nonwoven fabric per unit mass and is a value measured by a BET adsorption method using nitrogen as an adsorption gas. The specific surface area can be measured using, for example, Tristar 3000 apparatus manufactured by Micromeritics Japan, "Acusorb 2100" manufactured by Shimadzu Corp., or an apparatus having specifications equivalent thereto.

A larger specific surface area of the nonwoven fabric means that there is large area which can absorb cells and plasma proteins, etc., during blood processing using a filter element containing the nonwoven fabric in the same mass.

The airflow resistance of the nonwoven fabric contained in the filter element 5 of the present embodiment is preferably 25 Pa·s·m/g or larger and 100 Pa·s·m/g or smaller, more preferably 30 Pa·s·m/g or larger and 90 Pa·s·m/g or smaller, further preferably 40 Pa·s·m/g or larger and 80 Pa·s·m/g or smaller.

If the airflow resistance is smaller than 25 Pa·s·m/g, there is a tendency that the number of contacts with leukocytes is decreased so that the leukocytes are difficult to capture. If the airflow resistance of the nonwoven fabric is larger than 100 Pa·s·m/g, there is a tendency that clogging by blood cells is increased so that processing speed is decreased.

The airflow resistance of the nonwoven fabric of the present embodiment is a value measured as differential pressure generated when air flows at a predetermined flow rate in the nonwoven fabric, and is a value obtained by placing the nonwoven fabric on a vent hole of an air permeability testing apparatus (e.g., manufactured by Kato Tech Co., Ltd., KES-F8-AP1), measuring a pressure drop (Pa·s/m) generated when air is allowed to flow for approximately 10 seconds, and further dividing the obtained pressure drop by the basis weight ($g/m^2$) of the nonwoven fabric. In this respect, the measurement is performed for five samples cut out from different sites, and an average value thereof is used as the airflow resistance.

Higher airflow resistance of the nonwoven fabric means that air is less likely to penetrate the nonwoven fabric, and the fibers constituting the nonwoven fabric are entangled in a dense or uniform state, and indicates that the nonwoven fabric has the property of hindering a blood product from flowing. On the other hand, lower airflow resistance of the nonwoven fabric means that the fibers constituting the nonwoven fabric are entangled in a coarse or non-uniform state, and indicates that the nonwoven fabric has the property of facilitating the flow of a blood product.

The mean flow pore size of the nonwoven fabric contained in the filter element 5 of the present embodiment is preferably 1.0 μm or larger and 60 μm or smaller, more preferably 1.0 μm or larger and 30 μm or smaller, further preferably 1.0 μm or larger and 20 μm or smaller, particularly preferably 1.0 vim or larger and 8.0 μm or smaller. If the mean flow pore size is larger than 60 μm, there is a tendency that the frequency of contact with leukocytes is decreased so that removal performance for leukocytes and the like is reduced. If the mean flow pore size is smaller than 1.0 μm, there is a tendency that clogging by blood cells or pressure drop is increased so that blood products are less likely to flow to thereby decrease processing speed. The mean flow pore size is more preferably 1.5 μm or larger and 7.5 μm smaller, further preferably 2.5 μm or larger and 7.0 μm or smaller, particularly preferably 3.5 μm or larger and 6.5 μm or smaller, most preferably 4.5 μm or larger and 6.5 vm or smaller.

In the present embodiment, the mean flow pore size of the nonwoven fabric is a mean flow pore size (MFP) measured in accordance with ASTM F316-86 using a porometer (e.g., Perm Porometer CFP-1200AEXS (automatic pore size distribution measurement system for porous materials) manufactured by Porous Materials, Inc. (PMI) or Coulter R Porometer manufactured by Coulter Electronics, Inc.) and approximately 50 mg of a sample. A nonwoven fabric having a larger mean flow pore size facilitates the flow of a blood product, but reduces removal performance for leukocytes and the like. On the other hand, a nonwoven fabric having a smaller mean flow pore size improves removal performance for leukocytes and the like, but hinders a blood product from flowing and is also more likely to be clogged.

When the filter element of the present embodiment is constituted by a plurality of nonwoven fabrics, a plurality of nonwoven fabrics with different mean flow pore sizes may be stacked so that the mean flow pore sizes decrease from the inlet side toward the outlet side of the container.

If necessary, a pre-filter having a mean flow pore size of 50 μm or larger and 200 μm or smaller may be disposed closer to the inlet side than the filter element, for the main purpose of removing microaggregates, and a post-filter having a mean flow pore size of 50 μm or larger and 200 μm or smaller may be disposed closer to the outlet side than the filter element, for the main purpose of preventing drift.

The filter element of the present embodiment and the nonwoven fabric contained therein both have a porosity of preferably 65% or more and 90% or less, more preferably 75% or more and 88% or less.

If the porosity is less than 65%, there is a tendency that a filtration rate for blood and the like is reduced so that leukocyte removal requires a long time. If the porosity exceeds 90%, there is a tendency that high removal performance for leukocytes and the like is difficult to obtain because of a decrease in the enlaced parts between fibers which are easy for leukocytes to be adsorbed to.

In this context, the porosity (%) of the filter element (nonwoven fabric) refers to the volume percentage of space in the filter element (nonwoven fabric) and is, for example, a value calculated according to the following expression from a filter element (nonwoven fabric) volume per unit area of the filter element (nonwoven fabric) calculated from the thickness of the filter element (nonwoven fabric), and a resin volume per unit area of the filter element (nonwoven fabric) calculated from the basis weight (mass per unit area) of the filter element (nonwoven fabric) and the specific gravity of the resin constituting the filter element (nonwoven fabric):

$$\text{Porosity (\%)} = (1 - \text{Resin volume}/\text{Filter element (nonwoven fabric) volume}) \times 100$$

It is preferred that the filter element and the nonwoven fabric contained therein should maintain the porosity described above even in a packed and compressed state of the blood processing filter.

The filter element of the present embodiment may be constituted by one nonwoven fabric or may be constituted by a plurality of nonwoven fabrics. The filter element constituted by a plurality of nonwoven fabrics may be constituted by nonwoven fabrics of a single type or may be constituted by nonwoven fabrics of plural types. All of the plurality of nonwoven fabrics do not have to be the nonwoven fabrics defined in the present embodiment, and at least one of the nonwoven fabrics can be the nonwoven fabric according to the present embodiment. The nonwoven fabric according to the present embodiment preferably occupies 30% or more of the total thickness of the filter element. The occupancy is more preferably 40% or more, further preferably 50% or more.

When the filter element is constituted by nonwoven fabrics of plural types, it is preferred that the filter element should have a first nonwoven fabric layer which is disposed upstream and removes microaggregates, and a second nonwoven fabric layer which is disposed downstream of the first nonwoven fabric layer in order to remove leukocytes and the like. Each of the first and second nonwoven fabric layers may be one nonwoven fabric or may consist of a plurality of nonwoven fabrics. Each of the first and second nonwoven fabric layers each consisting of a plurality of nonwoven fabrics may be constituted by nonwoven fabrics of a single type or may be constituted by nonwoven fabrics of plural types.

The first nonwoven fabric layer disposed on the inlet side is preferably a nonwoven fabric layer consisting of a nonwoven fabric having an average fiber diameter of from 3 to 60 μm, from the viewpoint of aggregate removal.

The second nonwoven fabric layer is preferably a nonwoven fabric layer consisting of a nonwoven fabric having an average fiber diameter of from 0.3 to 3.0 μm from the viewpoint of removing leukocytes and the like.

A post-filter layer may be further disposed, if necessary, downstream of the second nonwoven fabric layer.

The number of nonwoven fabrics constituting each nonwoven fabric layer can be appropriately selected in consideration of removal performance for leukocytes and the like required for the blood processing filter, a processing time, or balance thereof, etc., and may be, for example, one sheet for each.

The first nonwoven fabric layer of the filter element in this form is disposed upstream (on the inlet side) of the second nonwoven fabric layer, and the nonwoven fabric constituting the second nonwoven fabric layer has a smaller average fiber diameter than that of the nonwoven fabric constituting the first nonwoven fabric layer. Even if aggregates are formed in blood, the loose nonwoven fabric of the upstream (inlet-side) first nonwoven fabric layer thereby captures the aggregates to decrease the number of aggregates arriving at the fine nonwoven fabric of the downstream second nonwoven fabric layer. Thus, the clogging of the filter material by aggregates is suppressed. Particularly, the nonwoven fabric constituting the first nonwoven fabric layer has an average fiber diameter of from 3 to 60 μm and is effective for suppressing the clogging of the filter element. Also, the nonwoven fabric of the second nonwoven fabric layer has an average fiber diameter of smaller than 3 μm and can prevent reduction in filtration performance (removal performance for leukocytes and the like).

The average fiber diameter of the nonwoven fabric constituting the first nonwoven fabric layer is more preferably from 4 to 40 μm, further preferably from 30 to 40 μm and/or from 10 to 20 μm, because the clogging of the filter element can be suppressed more reliably. The average fiber diameter of the nonwoven fabric constituting the second nonwoven fabric layer is preferably 0.3 μm or larger because clogging by leukocytes and the like and increase in pressure drop are prevented. The average fiber diameter is more preferably from 0.5 to 2.5 μm, further preferably from 0.7 μm to 1.5 μm, particularly, from the viewpoint of removal performance for leukocytes and the like, etc. The second nonwoven fabric layer may be configured such that a plurality of nonwoven fabrics with a different average fiber diameters are stacked so that the average fiber diameters decrease from the inlet side toward the outlet side.

A third nonwoven fabric layer consisting of a nonwoven fabric having an average fiber diameter of from 1.2 to 1.5 μm and/or from 0.9 to 1.2 μm may be further disposed for use downstream of the second nonwoven fabric layer.

The first nonwoven fabric layer containing a nonwoven fabric having a thick average fiber diameter and the second nonwoven fabric layer containing a nonwoven fabric having a thin average fiber diameter may be alternately arranged. In this case, it is preferred that they are arranged in alternative order of the first nonwoven fabric layer, the second nonwoven fabric layer, the first nonwoven fabric layer, the second nonwoven fabric layer, . . . from the inlet side, from the viewpoint of improvement in flowability by cascade structure formation.

The average fiber diameter according to the present embodiment refers to a value determined according to the following procedures:

Several points from a nonwoven fabric portion found to be substantially uniform of the nonwoven fabric actually constituting the filter element or one or more nonwoven fabrics having substantially the same quality thereof are selected as samples. Photographs showing images of diameters of fibers in the nonwoven fabric samples are taken using a scanning electron microscope.

A transparent sheet having grids is laid over the photograph thus obtained. The thicknesses (widths) of a total of 100 fibers overlapped with the grid intersections are measured as diameters by comparing them with the diameter of polystyrene latex having a known diameter, which is, as a control, allowed to appear in the photograph, or is photographed at the same magnification thereas, and an average value of the thicknesses is used as the average fiber diameter. In this context, the diameter refers to the width of the fiber in the direction perpendicular to the fiber axis. Here, when a plurality of fibers are overlapped so that the diameter of a fiber hidden behind another fiber cannot be measured, when a plurality of fibers are melted, for example, to form a thick fiber, when fibers significantly differing in diameter coexist, or when the boundary of the fibers is not clear, such data is not counted.

In the case where the filter element contains a plurality of nonwoven fabrics, if the measured average fiber diameter for each nonwoven fabric is evidently different, this means that these nonwoven fabrics are of different types. In this case, their average fiber diameters are separately measured again by finding the interface between the different nonwoven fabrics. In this context, the phrase "average fiber diameter is evidently different" refers to the case where a significant difference is statistically observed.

For a blood processing filter having a plate-like and soft container, particularly, a post-filter layer is preferably disposed downstream of the second nonwoven fabric layer, because the flow of blood is prevented from being inhibited in such a way that filter element is pressed against the outlet-side container due to positive pressure on the inlet side generated during filtration and further, the outlet-side container is tightly contacted with the filter element due to negative pressure on the outlet side, and also because the weldability between the soft container and the filter element is enhanced.

As the post-filter layer, a filtration medium known in the art, such as a fibrous porous medium (e.g., nonwoven fabrics, woven fabrics, and meshes), or a porous body having three-dimensional network continuous pores, can be employed. Examples of materials for these filtration media include polypropylene, polyethylene, styrene-isobutylene-styrene copolymers, polyurethane, and polyester. A post-filter layer made of a nonwoven fabric is preferred from the viewpoint of productivity and the welding strength of the blood processing filter. A post-filter layer having a plurality of protrusions by embossing or the like is particularly preferred because the flow of blood is rendered more uniform.

The surface of each nonwoven fabric constituting the filter element may be modified by a technique known in the art, such as coating, chemical treatment, or radiation treatment, for the purpose of controlling selective separation properties for blood cells, surface hydrophilicity, etc.

For more reliably suppressing the clogging of the filter element, the bulk density of the nonwoven fabric constituting the first nonwoven fabric layer is preferably from 0.05 to 0.50 $g/cm^3$ and may be more preferably from 0.10 to 0.40 $g/cm^3$. If the bulk density of the nonwoven fabric of the first nonwoven fabric layer exceeds 0.50 $g/cm^3$, the nonwoven fabric might be clogged by the capture of aggregates or leukocytes, resulting in a reduced filtration rate. On the other hand, if the bulk density falls below 0.05 $g/cm^3$, aggregate capture performance might be reduced so that the nonwoven fabric of the second nonwoven fabric layer is clogged, resulting in a reduced filtration rate. In addition, the mechanical strength of the nonwoven fabric may be reduced.

The "bulk density of the nonwoven fabric" is determined by cutting out samples with a size of 2.5 cm×2.5 cm from the nonwoven fabric at a site thought to be homogeneous, measuring the basis weight ($g/m^2$) and the thickness (cm) of the samples by methods mentioned later, and dividing the basis weight by the thickness. In this respect, the measurement of the basis weight and the thickness is performed for three samples cutout out from different sites and an average value thereof is used as the bulk density.

The basis weight of the nonwoven fabric is determined with a sample having a size of 2.5 cm×2.5 cm cut out from the nonwoven fabric at a site thought to be homogeneous, measuring the weight of the samples, and converting this weight to a mass per unit square meter. Also, the thickness of the nonwoven fabric is determined with a sample having a size of 2.5 cm×2.5 cm cut out from the nonwoven fabric at a site thought to be homogeneous, and measuring the thickness of its center (one site) by a constant-pressure thickness meter. The load pressure of the constant-pressure thickness meter is set to 0.4 N, and the area of the measurement part is set to 2 $cm^2$.

The bulk density of the nonwoven fabric constituting the second nonwoven fabric layer is preferably from 0.05 to 0.50 $g/cm^3$, more preferably from 0.07 to 0.40 $g/cm^3$, further preferably from 0.10 to 0.30 $g/cm^3$. If the bulk density of the nonwoven fabric of the second nonwoven fabric layer is larger than 0.50 $g/cm^3$, there is a tendency that the flow resistance of the nonwoven fabric is increased, and clogging by blood cells is accordingly increased so that processing speed is decreased. On the other hand, if the bulk density is smaller than 0.05 $g/cm^3$, there is a tendency that the frequency of contact with leukocytes is decreased so that the leukocytes are difficult to capture. In addition, the mechanical strength of the nonwoven fabric may be reduced.

In the present embodiment, the packing density of the filter element, which is the bulk density of the filter element when it is packed in the blood processing filter, is preferably 0.1 $g/cm^3$ or higher and 0.5 $g/cm^3$ or lower, more preferably 0.1 $g/cm^3$ or higher and 0.3 $g/cm^3$ or lowe. If the packing density of the filter element exceeds 0.5 $g/cm^3$, clogging by blood cells or pressure drop tends to be easily increased. If the packing density is lower than 0.1 $g/cm^3$, filtration performance (removal performance for leukocytes and the like) tends to be reduced.

The packing density can be determined, for example, according to Mass (g)/{Cut size ($cm^2$)×Thickness (cm)} by cutting the filter element into a packing cut size ($cm^2$), measuring its mass (g), filling this cut piece into an actual filter container, and measuring its thickness (cm) in a compressed state.

The nonwoven fabric more suitable for carrying out the present embodiment may be defined by a filling rate. The filling rate of the nonwoven fabric is calculated according to the following expression by measuring the area, thickness, and mass of the nonwoven fabric cut into an arbitrary dimension (nonwoven fabric in a state that is not filled in the filter) and the specific gravity of the material constituting the nonwoven fabric:

Filling rate=[Mass (g) of the nonwoven fabric/(Area ($cm^2$) of the nonwoven fabric×Thickness (cm) of the nonwoven fabric)]/Specific gravity ($g/cm^3$) of the material constituting the nonwoven fabric.

The filling rate of the nonwoven fabric constituting the first nonwoven fabric layer according to the present embodiment is preferably 0.04 or larger and 0.40 or smaller and may be more preferably 0.08 or larger and 0.30 or smaller. If the filling rate is larger than 0.40, there is a tendency that the flow resistance of the nonwoven fabric is increased by the capture of aggregates, leukocytes, and the like, and clogging by blood cells is accordingly increased so that processing speed is decreased. On the other hand, if the filling rate is smaller than 0.04, aggregate capture performance might be reduced so that the nonwoven fabric of the second nonwoven fabric layer is clogged, resulting in a reduced filtration rate. In addition, the mechanical strength of the nonwoven fabric may be reduced.

The filling rate of the nonwoven fabric constituting the second nonwoven fabric layer is preferably from 0.04 to 0.40 and may be more preferably from 0.06 to 0.30, further preferably from 0.08 to 0.22. If the filling rate of the nonwoven fabric of the second nonwoven fabric layer is larger than 0.40, there is a tendency that the flow resistance of the nonwoven fabric is increased, and clogging by blood cells is accordingly increased so that processing speed is decreased. On the other hand, if the filling rate is smaller than 0.04, there is a tendency that the frequency of contact with leukocytes and the like is decreased so that the leukocytes are difficult to capture. In addition, the mechanical strength of the nonwoven fabric may be reduced.

In the present embodiment, examples of the fiber material for the nonwoven fabric contained in the filter element may include, but are not limited to, polymer materials such as polyester, polyamide, polyacrylonitrile, polymethyl methacrylate, polyethylene, and polypropylene. Also, metal fibers may be partially used. Use of fibers made of such a synthetic polymer material in the filter element can prevent the degeneration of blood. More preferably, the respective nonwoven fabrics of the first nonwoven fabric layer and the second nonwoven fabric layer having a stable fiber diameter can be obtained by adopting fibers containing polyester. Among others, polyethylene terephthalate or polybutylene terephthalate is preferred because of having affinity for a blood product and stable wettability for blood.

In the present embodiment, the CWST (critical wetting surface tension) of the nonwoven fabric (or the nonwoven fabric coated with a coat layer) contained in the filter element is preferably 70 dyn/cm or larger, more preferably 85 dyn/cm or larger, further preferably 95 dyn/cm or larger. The nonwoven fabric having such a critical wetting surface tension secures stable wettability for blood and is thereby capable of efficiently removing leukocytes and the like while allowing platelets in a blood product to pass therethrough.

The CWST refers to a value determined according to the following method: aqueous solutions of sodium hydroxide, calcium chloride, sodium nitrate, acetic acid, or ethanol differing in concentration are prepared such that the surface tension varies by from 2 to 4 dyn/cm. The surface tension (dyn/cm) of each aqueous solution thus obtained is from 94 to 115 for the aqueous sodium hydroxide solutions, from 90 to 94 for the aqueous calcium chloride solutions, from 75 to 87 for the aqueous sodium nitrate solutions, 72.4 for pure water, from 38 to 69 for the aqueous acetic acid solutions, and from 22 to 35 for the aqueous ethanol solutions ("Kagaku Binran (Handbook of Chemistry in English), Basics II", revised 2nd edition, edited by The Chemical Society of Japan, Maruzen Publishing Co., Ltd., 1975, p. 164). Ten drops each of the thus-obtained aqueous solutions having different surface tension by from 2 to 4 dyn/cm are placed on the nonwoven fabric in ascending order of surface tension, and left for 10 minutes. The case where 9 or more out of the 10 drops left for 10 minutes are absorbed by the nonwoven fabric is determined to be a wet state, while the case where less than 9 out of the 10 drops are absorbed is determined to be a non-wet state. In this way, the liquids are assayed on nonwoven fabric in ascending order of surface tension. During this assay, the determination changes from the wet state to the non-wet state. In this respect, the CWST value of the nonwoven fabric is defined as an average value of the surface tension value of the last liquid for which the wet state is observed and the surface tension value of the first liquid for which the non-wet state is observed. For example, the CWST value of the nonwoven fabric that is wet by a liquid having a surface tension of 64 dyn/cm and is non-wet by a liquid having a surface tension of 66 dyn/cm is 65 dyn/cm.

The steam heat treatment may be performed at a high temperature (e.g., 110° C. or higher) or high pressure in order to obtain a higher sterilizing effect. It has been revealed that during such high-pressure steam sterilization treatment, removal performance for leukocytes and the like is more easily reduced because the blood processing filter is exposed to higher pressure and heat as compared with usual steam heat treatment.

In this respect, Japanese Patent Publication No. 8-6239 discloses a material that can maintain high compressibility or bulkiness after high-pressure steam sterilization and thereby maintain favorable blood filtration performance. Also, Japanese Patent No. 4565762 discloses a method for preventing removal performance for leukocytes and the like from being reduced due to the separation of a surface polymer from a filter material during high-pressure steam sterilization treatment.

However, both of these approaches merely focus on reduction in the performance of the filter element used alone. These approaches do not reduce change in physical properties or performance caused by high-pressure steam sterilization after the filter element is actually installed in a filter container and held by the holding parts of the container or its periphery is welded to the container. Thus, the approaches are not sufficiently effective for reduction in the performance of a filter itself.

The present inventor has found that provided that the heat shrinkage rate of the nonwoven fabric constituting the filter element and its elongation rates in predetermined directions fall within predetermined ranges, a filter for blood processing with a reduced degradation of filtration performance even after high-pressure steam sterilization under more severe conditions can be provided.

From these viewpoints, in the present embodiment, the heat shrinkage rate of the nonwoven fabric contained in the filter element is preferably 5% or more and 24% or less, more preferably 10% or more and 20% or less, further preferably 10% or more and 15% or less.

If the heat shrinkage rate of the nonwoven fabric exceeds 24%, the nonwoven fabric contracts drastically after high-pressure steam sterilization and reduces filtration performance (leukocyte removal performance). Specifically, a higher heat shrinkage rate of the nonwoven fabric largely changes the shape of the fibers constituting the nonwoven fabric after high-pressure steam sterilization, accordingly decreasing the specific surface area of the nonwoven fabric. Due to this influence, filtration performance (removal performance for leukocytes and the like) is relatively reduced. On the contrary, a filtration time tends to be shortened because resistance is decreased.

However, it has been revealed that if the heat shrinkage rate of the nonwoven fabric is too small (specifically, less than 5%), a container may fail to properly hold the filter element at the time of assembling of a filter due to a reduced elongation rate, whereby the leak of blood and the like may occur to facilitate reduction in filtration performance.

In this context, the heat shrinkage rate of the nonwoven fabric refers to an average value of the ratios (%) of the respective differences in the lengths of central portions in the X and Y directions between before and after dry heat treatment at 140° C. for 1 minute to the original lengths, as to a 30 cm square cut out of the nonwoven fabric.

The elongation rates of the nonwoven fabric both in a direction where the elongation rate is maximized and in a direction vertical thereto upon packing of a filter are preferably 1% or more and 3% or less, more preferably 1.5% or more and 2.5% or less. The difference between the elongation rate in the direction where the elongation rate is maximized and the elongation rate in the direction vertical thereto is preferably 1% or less.

If any of the elongation rates in a direction where the elongation rate is maximized and in a direction vertical thereto is 1% or less, the filter element may not be compressed at a sufficiently high density at the filter element holding part or welded part of the container at the time of assembling of a filter. Thus, the filter may be insufficiently assembled, or side flow may occur in which blood leaks over the outer edges of the filter element and passes without being filtered.

If any of the elongation rates in a direction where the elongation rate is maximized and in a direction vertical thereto exceeds 3%, the filter element is significantly deformed during high-pressure steam sterilization treatment or during filtration to thereby reduce blood filtration performance.

The difference between the elongation rate in the direction where the elongation rate is maximized and the elongation rate in the direction vertical thereto is preferably 1% or less, more preferably 0.5% or less. If this difference exceeds 1%, there is a tendency that the degree of filter element compression is non-uniform at or near the filter element holding part or the filter element welded part of the container at the time of molding of a filter to thereby reduce blood filtration performance.

In this context, the elongation rate refers to the ratio (%) of the elongation of the nonwoven fabric before steam heat treatment under a tensile load of 0.26 N/cm to the original length.

A general nonwoven fabric has the maximum elongation rate in the direction vertical to the winding direction of a raw fabric. Thus, when the directions of the nonwoven fabric contained in the filter element are known, the direction where the elongation rate of the nonwoven fabric is maximized can be determined on the basis of the directions.

As mentioned above, a nonwoven fabric that satisfies the condition that the quantity of crystallization heat of the uncrystallized portion is 5 J/g or smaller as well as the condition that the heat shrinkage rate is from 5 to 24%, and the elongation rates both in a direction where the elongation rate is maximized and in a direction vertical thereto are 1% or more and 3% or less can be used as the nonwoven fabric constituting the filter element to thereby provide a blood processing filter that further withstands steam heat treatment and neither influences on filter assemblability nor reduces filtration performance after high-pressure steam sterilization treatment.

The nonwoven fabric contained in the filter element of the present embodiment is not limited by its production method. The nonwoven fabric used in the present embodiment has high crystallinity. Such a nonwoven fabric can be produced by any of wet and dry methods. In the present embodiment, the nonwoven fabric is particularly preferably produced by a melt blown method because a nonwoven fabric having the optimum formation index and average fiber diameter is stably obtained.

One example of the melt blown method will be described as the method for producing the nonwoven fabric used in the present embodiment. In the melt blown method, a molten polymer fluid obtained by melting in an extruder is filtered through an appropriate filter, then introduced to a molten polymer inlet of a melt blown die, and then discharged from an orifice nozzle. At the same time therewith, a heated gas introduced to a heated gas inlet is introduced to a heated gas ejection slit formed from the melt blown die and a lip, and ejected therefrom so that the discharged molten polymer is attenuated to form ultrathin fibers. The formed ultrathin fibers are laminated to thereby obtain a nonwoven fabric. The nonwoven fabric can be further heat-treated using a heat suction drum, a hot plate, hot water, a hot air heater, etc. to obtain a nonwoven fabric having the desired crystallinity.

In this respect, for applying thereto a necessary and sufficient quantity of heat, it is desirable to adjust the heating temperature and time according to the properties of the polymer. For producing the nonwoven fabric having high crystallinity used in the present embodiment, it is preferred that the temperature of the heat source should be a temperature equal to or higher than [melting point of the polymer—120]° C., more preferably from [melting point of the polymer—20]° C. to [melting point of the polymer—60]° C. The heating time varies depending on the heating temperature and is preferably at least 3 seconds or longer, more preferably 10 seconds or longer, further preferably 20 seconds or longer, particularly preferably 30 seconds or longer.

If the temperature of the heat source is lower than [melting point of the polymer—120]° C. or if the heating time is shorter than 3 seconds, this is not preferred because the crystallinity of the polymer to be satisfied tends to be difficult to obtain. As one example, a sufficient quantity of heat suitable for the present embodiment can be applied thereto by allowing the polybutylene terephthalate nonwoven fabric after spinning to stay in dry air of 140° C. for 120 seconds.

Examples of the material for the container which houses the filter element include, but are not limited to, resins. In this case, any of rigid resins and soft resins may be used.

Examples of the rigid resin material include phenol resin, acrylic resin, epoxy resin, formaldehyde resin, urea resin, silicon resin, ABS resin, nylon, polyurethane, polycarbonate, vinyl chloride, polyethylene, polypropylene, polyester, and styrene-butadiene copolymers.

The soft resin material for the container is preferably similar in thermal and electrical properties to the filter element. Examples of suitable materials include: thermoplastic elastomers such as soft polyvinyl chloride, polyurethane, ethylene-vinyl acetate copolymers, polyolefins such as polyethylene and polypropylene, hydrogenation products of styrene-butadiene-styrene copolymers, and styrene-isoprene-styrene copolymers or hydrogenation products thereof; and mixtures of the thermoplastic elastomers with softening agents such as polyolefins and ethylene-ethyl acrylate. The material is preferably soft vinyl chloride, polyurethane, an ethylene-vinyl acetate copolymer, a polyolefin, or a thermoplastic elastomer composed mainly of any of them, more preferably soft vinyl chloride or a polyolefin.

The shape of the container is not particularly limited as long as the shape has an inlet for a liquid to be processed (leukocyte-containing liquid) and an outlet for a processed (leukocyte-free) liquid. The shape is preferably adapted to the shape of the filter element.

When the filter element is, for example, plate-like, the container can have a flat shape consisting of a polygon such as a tetragon or a hexagon, a circle, an ellipse, or the like according to the plate-like shape. More specific examples thereof include configuration in which, as shown in FIG. 1 or 2, the container 1 is constituted by an inlet-side container member having the first port 3 as a liquid inlet/outlet and an outlet-side container member having the second port 4 as a liquid inlet/outlet, and both the container members sandwich the filter element 5 either directly or via a support such that the inside of the filter is divided into two rooms to form the flat blood processing filter 10.

As another example, when the filter element is cylindrical, it is preferred that the container should also be cylindrical. More specifically, the container is constituted by a tubular barrel which houses the filter element, an inlet-side header having a liquid inlet, and an outlet-side header having a liquid outlet, and preferably has a shape in which the inside of the container is divided into two spaces by potting such that a liquid introduced from the inlet flows from the outer periphery to the inner periphery (or from the inner periphery to the outer periphery) of the cylindrical filter, to form the cylindrical blood processing filter.

Alternatively, for example, a member made of a soft material, such as a flexible synthetic resin sheet, provided with an inlet and an outlet may be used. The filter element may be sandwiched or wrapped by this member, and then the periphery of the filter element can be welded to the soft material member to prepare a container.

In the case of using the container as shown in FIG. 1, the ratio of the thickness of the filter element after being incorporated in the inside of the filter, i.e., the thickness of the filter element sandwiched between the holding parts (convex parts) respectively disposed in the inlet-side container member and the outlet-side container member, to the thickness of the filter element before the incorporation is preferably from 0.5 to 0.55. It is also preferred that the filter element should be cut such that the distances between the convex parts and the outer peripheral end parts of the filter element (lengths of protruding parts of the filter element) are from 3 to 4 mm.

If the packing density of the filter element in the filter having such configuration is lower than 0.1 g/cm$^3$, removal performance for leukocytes and the like may be reduced because the filter element, when containing a nonwoven fabric having a high heat shrinkage rate, is dislocated from or drops out of the holding parts of the container after steam heat treatment and thus cannot be effectively used. On the other hand, if the nonwoven fabric constituting the filter element has a low heat shrinkage rate, there is a tendency that the filter element is difficult to deform to thereby reduce an elongation rate. The low elongation rate makes it difficult to sufficiently compress the filter element holding parts of the container at the time of assembling a filter. Thus, defects may arise easily in such a way that the container fails to sufficiently hold the filter element, or blood leaks to the outside from the assembled filter.

In the case of using a soft member as the material for the container and welding this soft member and the filter element at the periphery of the filter element, blood is filtered by flowing in the filter element on the internal side of the welded part. At the time of assembling of a filter, the sealing performance between the soft member and the filter element is generally enhanced by pushing the filter element into the soft member while melting the soft member and the filter element. For such preparation, it is preferred that the ratio of the filter element thickness at the welded part after welding to the filter element thickness before the welding should be from 0.15 to 0.20.

If the nonwoven fabric contained in the filter element having such configuration has a high heat shrinkage rate, the filter element is significantly deformed after steam heat treatment (particularly, high-pressure steam sterilization) because the welded part is fixed. This renders blood flow non-uniform in the filter and reduces blood filtration performance. If the nonwoven fabric contained in the filter element has a low heat shrinkage rate and the filter element has a low elongation rate, the welded part between the soft member and the filter element cannot be sufficiently compressed at the time of assembling a filter. Thus, defects arise in such a way that the filter cannot be assembled, or blood leaks to the outside from the assembled filter.

Next, a leukocyte removal method using the blood processing filter of the present embodiment will be described.

The leukocyte removal method of the present embodiment comprises the step of allowing a leukocyte-containing liquid to pass through a blood processing filter having a filter element containing a nonwoven fabric housed in a container, to remove leukocytes from the leukocyte-containing liquid.

In this context, the leukocyte-containing liquid collectively includes body fluids and synthetic blood containing leukocytes, and specific examples include whole blood and a liquid consisting of a single or plural types of blood components obtained by preparation from whole blood, such as whole blood, a concentrated red cell solution, a washed red cell suspension, a thawed red cell concentrate, synthetic blood, platelet-poor plasma (PPP), platelet-rich plasma (PRP), plasma, frozen plasma, a platelet concentrate, and buffy coat (BC); a solution in which an anticoagulant, a preservative solution, or the like is added thereto; or a blood product such as a whole blood product, a red cell product, a platelet product, or a plasma product. The whole blood product is a whole blood product containing whole blood supplemented with an additive, for example, a preservative solution or an anticoagulant, such as citrate phosphate dextrose (CPD), citrate phosphate dextrose adenine-1 (CPDA-1), citrate phosphate-2-dextrose (CP2D), acid citrate dextrose formula-A (ACD-A), acid citrate dextrose formula-B (ACD-B), or heparin.

Furthermore, a liquid obtained by processing the liquid mentioned above by the method of the present embodiment is referred to as a leukocyte-free liquid.

Hereinafter, one mode of a method for preparing each blood product by removing leukocytes by the leukocyte removal method will be described.

(Preparation of Leukocyte-Free Whole Blood Product)

The leukocyte-free whole blood product can be obtained by providing a whole blood product by the addition of, for example, a preservative solution or an anticoagulant, such as citrate phosphate dextrose (CPD), citrate phosphate dextrose adenine-1 (CPDA-1), citrate phosphate-2-dextrose (CP2D), acid citrate dextrose formula-A (ACD-A), acid citrate dextrose formula-B (ACD-B), or heparin, to collected whole blood, and then removing leukocytes from the whole blood product using the blood processing filter of the present embodiment.

In the preparation of the leukocyte-free whole blood product, in the case of leukocyte removal before preservation, the whole blood preserved at room temperature or under refrigeration can be subjected to leukocyte removal using the blood processing filter at room temperature or under refrigeration preferably within 72 hours, more preferably within 24 hours, particularly preferably within 12 hours, most preferably within 8 hours after blood collection to obtain the leukocyte-free whole blood product. In the case of leukocyte removal after preservation, leukocytes can be removed from the whole blood preserved at room temperature, under refrigeration, or under freezing, preferably within 24 hours before use, using the blood processing filter to obtain the leukocyte-free whole blood product.

(Preparation of Leukocyte-Free Red Cell Product)

A preservative solution or an anticoagulant, such as CPD, CPDA-1, CP2D, ACD-A, ACD-B, or heparin, is added to collected whole blood. A separation method for each blood component includes the case of performing centrifugation after removal of leukocytes from the whole blood, and the case of removing leukocytes from red cells or red cells and BC after centrifugation of the whole blood.

In the case of performing centrifugation after removal of leukocytes from the whole blood, the leukocyte-free red cell product can be obtained by centrifuging the leukocyte-free whole blood.

In the case of centrifuging the whole blood before leukocyte removal, the centrifugation conditions are divided into two types: soft spin conditions where the whole blood is separated into red cells and PRP, and hard spin conditions where the whole blood is separated into red cells, BC, and PPP. After addition of a preservative solution such as SAGM, AS-1, AS-3, AS-5, or MAP, if necessary, to red cells separated from the whole blood or red cells containing BC, leukocytes can be removed from the red cells using the leukocyte removal filter to obtain the leukocyte-free red cell product.

In the preparation of the leukocyte-free red cell product, the whole blood preserved at room temperature or under refrigeration can be centrifuged preferably within 72 hours, more preferably within 48 hours, particularly preferably within 24 hours, most preferably within 12 hours after blood collection.

In the case of leukocyte removal before preservation, leukocytes can be removed from the red cell product preserved at room temperature or under refrigeration, preferably within 120 hours, more preferably within 72 hours, particularly preferably within 24 hours, most preferably within 12 hours after blood collection, using the blood processing filter at room temperature or under refrigeration to obtain the leukocyte-free red cell product. In the case of leukocyte removal after preservation, leukocytes can be removed from the red cell product preserved at room temperature, under refrigeration, or under freezing, preferably within 24 hours before use, using the blood processing filter to obtain the leukocyte-free red cell product.

(Preparation of Leukocyte-Free Platelet Product)

A preservative solution or an anticoagulant, such as CPD, CPDA-1, CP2D, ACD-A, ACD-B, or heparin, is added to collected whole blood.

A separation method for each blood component includes the case of performing centrifugation after removal of leukocytes from the whole blood, and the case of removing leukocytes from PRP or platelet after centrifugation of the whole blood.

In the case of performing centrifugation after removal of leukocytes from the whole blood, the leukocyte-free platelet product can be obtained by centrifuging the leukocyte-free whole blood.

In the case of centrifuging the whole blood before leukocyte removal, the centrifugation conditions are divided into two types: soft spin conditions where the whole blood is separated into red cells and PRP, and hard spin conditions where the whole blood is separated into red cells, BC, and PPP. Under the soft spin conditions, leukocytes are removed from PRP separated from the whole blood with the blood processing filter, and then, the leukocyte-free platelet product is obtained by centrifugation, or platelet and PPP are obtained by centrifuging PRP, and then, leukocytes can be removed with the blood processing filter to obtain the leukocyte-free platelet product. Under the hard spin conditions, a pool of one unit or several to dozen units of BC separated from the whole blood is supplemented, if necessary, with a preservative solution, plasma, or the like, and centrifuged to obtain platelet, and leukocytes can be removed from the obtained platelet with the blood processing filter to obtain the leukocyte-free platelet product.

In the preparation of the leukocyte-free platelet product, the whole blood preserved at room temperature is centrifuged preferably within 24 hours, more preferably within 12 hours, particularly preferably within 8 hours after blood collection. In the case of leukocyte removal before preservation, leukocytes can be removed from the platelet product preserved at room temperature, preferably within 120 hours, more preferably within 72 hours, particularly preferably within 24 hours, most preferably within 12 hours after blood collection, using the blood processing filter at room temperature to obtain the leukocyte-free platelet product. In the case of leukocyte removal after preservation, leukocytes can be removed from the platelet product preserved at room temperature, under refrigeration, or under freezing, preferably within 24 hours before use, using the blood processing filter to obtain the leukocyte-free platelet product.

(Preparation of Leukocyte-Free Plasma Product)

A preservative solution or an anticoagulant, such as CPD, CPDA-1, CP2D, ACD-A, ACD-B, or heparin, is added to collected whole blood.

A separation method for each blood component includes the case of performing centrifugation after removal of leukocytes from the whole blood, and the case of removing leukocytes from PPP or PRP after centrifugation of the whole blood.

In the case of performing centrifugation after removal of leukocytes from the whole blood, the leukocyte-free plasma product can be obtained by centrifuging the leukocyte-free whole blood.

In the case of centrifuging the whole blood before leukocyte removal, the centrifugation conditions are divided into two types: soft spin conditions where the whole blood is separated into red cells and PRP, and hard spin conditions where the whole blood is separated into red cells, BC, and PPP. Under the soft spin conditions, leukocytes are removed from PRP with the blood processing filter, and then, the leukocyte-free plasma product is obtained by centrifugation, or PRP is centrifuged into PPP and platelet, and then, leukocytes can be removed with the blood processing filter to obtain the leukocyte-free plasma product. Under the hard spin conditions, leukocytes can be removed from PPP with the blood processing filter to obtain the leukocyte-free plasma product.

In the preparation of the leukocyte-free plasma product, the whole blood preserved at room temperature or under refrigeration can be centrifuged preferably within 72 hours, more preferably within 48 hours, particularly preferably within 24 hours, most preferably within 12 hours after blood collection. Leukocytes can be removed from the plasma product preserved at room temperature or under refrigeration, preferably within 120 hours, more preferably within 72 hours, particularly preferably within 24 hours, most preferably within 12 hours after blood collection, using the blood processing filter at room temperature or under refrigeration to obtain the leukocyte-free plasma product. In the case of leukocyte removal after preservation, leukocytes can be removed from the plasma product preserved at room temperature, under refrigeration, or under freezing, preferably within 24 hours before use, using the blood processing filter to obtain the leukocyte-free plasma product.

Any mode such as a mode of collecting blood with a blood collection needle connected with a container for whole blood, and connecting the container containing whole blood or blood components after centrifugation with the blood processing filter, followed by leukocyte removal, a mode of collecting blood using a circuit in which at least a blood collection needle, a blood container, and the blood processing filter are sterilely connected, and performing leukocyte removal before centrifugation or after centrifugation, or a mode of connecting the blood processing filter with a container containing blood components obtained in an automatic blood collection apparatus or using the blood processing filter connected in advance with the container to perform leukocyte removal may be used as a mode from blood collection to the preparation of a leukocyte-free blood product, though the present embodiment is not limited by these modes. Alternatively, the leukocyte-free red cell product, the leukocyte-free platelet product, or the leukocyte-free plasma product may be obtained by centrifuging whole blood into each component in an automatic blood component collection apparatus, if necessary adding a preservative solution, and immediately thereafter allowing any of red cells, BC-containing red cells, BC, platelet, PRP, and PPP to pass through the blood processing filter to remove leukocytes.

The method of the present embodiment has higher leukocyte removal performance for all types of blood described above and is effective for shortening a processing time without causing clogging. The method of the present embodiment is particularly suitable for processing a red cell-containing solution, which is prone to extend a blood processing time.

In the preparation of these blood products, the leukocyte removal may be performed by allowing the leukocyte-containing blood to flow from a container located at a position higher than the blood processing filter into the blood processing filter via a tube, or by allowing the leukocyte-containing blood to flow by increasing pressure from the inlet side of the blood processing filter and/or reducing pressure from the outlet side of the blood processing filter using means such as a pump.

Hereinafter, a leukocyte removal method using the blood processing filter for extracorporeal circulation therapy will be described.

The inside of the blood processing filter is primed with physiological saline or the like, which is then replaced with a solution containing an anticoagulant such as heparin, nafamostat mesilate, ACD-A, or ACD-B. While the anticoagulant is added to blood diverted outside the body, the blood is injected into the inlet of the blood processing filter from a circuit connected with a human at a flow rate of from 10 to 200 mL/min, and leukocytes can be removed with the blood processing filter.

In the initial period of leukocyte removal (throughput: from 0 to 0.5 L), the flow rate is preferably from 10 to 50 mL/min, more preferably from 20 to 40 mL/min. After the initial period of leukocyte removal (throughput: from 0.2 to 12 L), the blood is preferably processed at a flow rate of from 30 to 120 mL/min, more preferably from 40 to 100 mL/min, particularly preferably from 40 to 60 mL/min. It is preferred to substitute the inside of the blood processing filter with physiological saline or the like after the leukocyte removal to return the blood, because the blood within the blood processing filter is not wasted.

In the present embodiment, the blood processing filter can remove 99% or more, more preferably 99.9% or more, further preferably 99.99% or more, of the number of leukocytes in blood (product) by the filtration of the blood (product).

In terms of a leukocyte residual rate, a value calculated according to the following expression preferably indicates removal performance of $1.0\times10^{-2}$ or less, more preferably removal performance of $1.0\times10^{-3}$ or less, further preferably removal performance of $1.0\times10^{-4}$ or less:

Leukocyte residual rate=[Leukocyte concentration (number/μL) (post-filtration blood)]/[Leukocyte concentration (number/μL) (pre-filtration blood)]

EXAMPLES

Hereinafter, the present invention will be described with reference to Examples. However, the present invention is not intended to be limited by these Examples.

Physical properties, etc. in Examples and Comparative Examples were measured by the methods given below.

(Heat Shrinkage Rate of Nonwoven Fabric)

For the heat shrinkage rate of the nonwoven fabric, three 30 cm×30 cm square samples cut out of a raw nonwoven fabric were prepared. The X and Y directions were determined, and the respective lengths of central portions in these directions were measured. After dry heat treatment at 140° C. for 1 minute, the lengths of the central parts were measured again. Values were determined by calculation according to the following expression, and an average value of the shrinkage rates in the X and Y directions was used as the heat shrinkage rate:

Heat shrinkage rate=((Length before the dry heat treatment−Length after the dry heat treatment)/Length before the dry heat treatment)×100(%)

(Specific Surface Area of Nonwoven Fabric)

The specific surface area ($m^2/g$) of the nonwoven fabric was determined by the gas adsorption method (BET method) using "Acusorb 2100" manufactured by Shimadzu Corp.

Specifically, the nonwoven fabric having a weight of from 0.50 g to 0.55 g was weighed and placed into a sample tube. After deaeration treatment at reduced pressure of $1\times10^{-4}$ mmHg (at room temperature) for 20 hours in the main body of Acusorb, krypton gas having a known occupied adsorption area was used as an adsorption gas and adsorbed onto the surface of the nonwoven fabric at the temperature of liquid nitrogen. The total surface area in the weighed nonwoven fabric was determined from the amount of the gas adsorbed, and divided by the mass of the weighed nonwoven fabric to determine a specific surface area.

(Measurement of Average Fiber Diameter)

Photographs of the nonwoven fabric were taken at 5 random sites per nonwoven fabric under an electron microscope. A transparent sheet having grids was laid over the photograph thus taken. The diameters of fibers at a total of 100 sites overlapped with the grid intersections were measured by comparing them with the diameter of polystyrene latex having a known diameter, which is a control, and an average thereof was calculated and used as the average fiber diameter.

(Elongation Rate of Nonwoven Fabric)

For the elongation rate measurement of the nonwoven fabric to be filled in a filter container (before steam heat treatment) (nonwoven fabric B as to Examples 21 to 26 and 31 to 36 and Comparative Examples 22 to 27), three samples of the nonwoven fabric cut into a width of 5 cm and a length of 30 cm were prepared and assayed.

Specifically, the sample was loaded in a universal autograph tester (model AG-1, manufactured by Shimadzu Corp.). The distance between chucks was set to 20 cm, and the nonwoven fabric was gradually pulled in the length direction. After pulling with a force of 2 N (0.26 N/cm), the distance between chucks was measured, and an average value thereof was determined. The elongation rate (%) was determined according to the following expression:

Elongation rate=((Average distance between chucks after the pulling−20)/20)×100(%)

A nonwoven fabric generally has the maximum elongation rate in the transverse direction (direction vertical to the winding direction of a raw nonwoven fabric (longitudinal direction of the nonwoven fabric)). Thus, in measuring the elongation rate of the nonwoven fabric, the transverse direction of the nonwoven fabric was determined as the direction where the elongation rate was maximized.

(Leukocyte Removal Performance Evaluation)

The blood used in evaluation was whole blood prepared by adding 70 mL of an anticoagulant CPD solution to 500 mL of blood immediately after blood collection, mixing them, and leaving the mixture standing for 2 hours. Hereinafter, this blood prepared for evaluation is referred to as pre-filtration blood.

A blood bag packed with the pre-filtration blood was connected with the inlet of the filter through a 40 cm polyvinyl chloride tube having an inside diameter of 3 mm and an outside diameter of 4.2 mm. Further, a blood bag for recovery was similarly connected with the outlet of the filter via a 60 cm polyvinyl chloride tube having an inside diameter of 3 mm and an outside diameter of 4.2 mm. Then, the pre-filtration blood was allowed to flow from the bottom of the blood bag packed with the pre-filtration blood into the filter by means of the 100 cm difference in height. The filtration time was measured until the amount of the blood flowing into the recovery bag became 0.5 g/min.

3 mL of blood (hereinafter, referred to as post-filtration blood) was further recovered from the recovery bag. The leukocyte removal performance was evaluated by determining a leukocyte residual rate. The leukocyte residual rate was calculated according to the following expression by measuring the number of leukocytes in the pre-filtration blood and the post-filtration blood using flow cytometry (apparatus: FACSCanto manufactured by Becton, Dickinson and Company):

Leukocyte residual rate=[Leukocyte concentration (number/μL) (post-filtration blood)]/[Leukocyte concentration (number/μL) (pre-filtration blood)].

The measurement of the number of leukocytes was performed by sampling 100 μL of each blood and using Leucocount kit (Becton, Dickinson and Company, Japan) containing beads for measurement by flow cytometry (apparatus: FACSCalibur manufactured by Becton, Dickinson and Company).

In the case of conducting evaluation under the filter shape of Examples 1 to 18 conditions described above (64 sheets of the nonwoven fabric, effective filtration area: 45 $cm^2$), a leukocyte removal filter element that can achieve a filtration time of 30 minutes or shorter and a leukocyte residual rate of $10.0\times10^{-3}$ or less is regarded as being practically desirable. Since, at a leukocyte residual rate of $10^{-4}$ or less, the number of residual leukocytes is close to the measurement limit, the filter shape conditions were set as described above so as to attain the leukocyte residual rate of $10^{-4}$ or less. A filter element having performance that satisfies the filtration time of 30 minutes or shorter and the leukocyte residual rate of $10.0\times10^{-3}$ or less under the conditions described above can achieve a filter with a leukocyte residual rate of from $10^{-4}$ to $10^{-6}$ which is necessary for preventing severe adverse reactions, when it is designed suitably for actual use.

<Case where Filter Element was Constituted by Plurality of Nonwoven Fabrics of Same Type>

Example 1

(Preparation of Nonwoven Fabric)

The nonwoven fabric used was a nonwoven fabric having a basis weight of 22 $g/m^2$, a thickness of 0.13 mm, a filling rate of 0.12, an average fiber diameter of 1.0 μm, a quantity of crystallization heat of the uncrystallized portion of 0.1 J/g before steam heat treatment, and a quantity of heat of crystal melting of 45 J/g and was prepared by a method of spinning polyethylene terephthalate (hereinafter, abbreviated to PET) by the melt blown method to form a fiber assembly, followed by the dry heat treatment of the obtained fiber assembly at 140° C. for 120 seconds. The crystallinity of the nonwoven fabric was measured by DSC using TA-60WS system manufactured by Shimadzu Corp. The X-ray crystallinity was 57%.

The nonwoven fabric was further coated with a hydrophilic polymer by a method described below.

A copolymer of 2-hydroxyethyl methacrylate (hereinafter, abbreviated to HEMA) and diethylaminoethyl methacrylate (hereinafter, abbreviated to DEAMA) was synthesized by conventional solution radical polymerization. The polymerization reaction was performed at a monomer concentration of 1 mol/L in ethanol at 60° C. for 8 hours in the presence of 1/200 mol of azoisobutyronitrile (AIBN) as an initiator. The nonwoven fabric was dipped in the ethanol solution of the obtained hydrophilic polymer. The absorbed redundant polymer solution was squeezed out of the nonwoven fabric removed from the polymer solution, and the polymer solution was dried off while dry air was sent, to form a coat layer covering the surface of the nonwoven fabric. The molar ratio of the nonionic hydrophilic group to the basic nitrogen-containing functional group in the surface portion (surface portion of the coat layer) of the nonwoven fabric coated with the polymer coat layer was 32.3. The mass of the coat layer per gram of the nonwoven fabric coated with the polymer coat layer was 9.0 mg/g (nonwoven fabric+coat layer). The CWST value was 100 dyn/cm.

(Preparation of Filter for Blood Processing)

A rigid container having an effective filtration area of 45 $cm^2$ was packed with 64 sheets of the obtained nonwoven fabric coated with the coat layer, and ultrasonic welding was conducted to prepare a filter.

This filter was steam heat-treated at 115° C. for 240 minutes and then vacuum-dried at 40° C. for 15 hours or longer to prepare a steam heat-treated filter.

As a result, the leukocyte residual rate was $0.7\times10^{-3}$, and the filtration time was 20 minutes, demonstrating low blood process pressure and high leukocyte removal performance.

Example 2

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 55 J/g. The X-ray crystallinity was 69%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 100 dyn/cm.

A filter was prepared in the same way as in Example 1 using this nonwoven fabric thus polymer-coated and subjected to the blood test.

As a result, the leukocyte residual rate was $0.3\times10^{-3}$, and the filtration time was 18 minutes, demonstrating low blood process pressure and high leukocyte removal performance.

Example 3

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 4.7 J/g, and a quantity of heat of crystal melting of 47 J/g. The X-ray crystallinity was 58%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 100 dyn/cm.

A filter was prepared in the same way as in Example 1 using this nonwoven fabric thus polymer-coated and subjected to the blood test.

As a result, the leukocyte residual rate was $5.3\times10^{-3}$, and the filtration time was 19 minutes, demonstrating low blood process pressure and high leukocyte removal performance.

Example 4

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 4.8 J/g, and a quantity of heat of crystal melting of 53 J/g. The X-ray crystallinity was 68%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 100 dyn/cm.

A filter was prepared in the same way as in Example 1 using this nonwoven fabric thus polymer-coated and subjected to the blood test.

As a result, the leukocyte residual rate was $4.3\times10^{-3}$, and the filtration time was 17 minutes, demonstrating low blood process pressure and high leukocyte removal performance.

Example 5

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 45 J/g. The X-ray crystallinity was 57%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $3.3\times10^{-3}$, and the filtration time was 23 minutes, demonstrating low blood process pressure and high leukocyte removal performance.

Example 6

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 55 J/g. The X-ray crystallinity was 69%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $2.8\times10^{-3}$, and the filtration time was 21 minutes, demonstrating low blood process pressure and high leukocyte removal performance.

Example 7

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 4.7 J/g, and a quantity of heat of crystal melting of 47 J/g. The X-ray crystallinity was 58%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $8.3\times10^{-3}$, and the filtration time was 22 minutes, demonstrating low blood process pressure and high leukocyte removal performance.

Example 8

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 4.8 J/g, and a quantity of heat of crystal melting of 53 J/g. The X-ray crystallinity was 68%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $7.3\times10^{-3}$, and the filtration time was 18 minutes, demonstrating low blood process pressure and high leukocyte removal performance.

Example 9

The nonwoven fabric used was made of polybutylene terephthalate (hereinafter, abbreviated to PBT) fibers and had a basis weight of 22 g/m$^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 45 J/g. The X-ray crystallinity was 58%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 98 dyn/cm.

A filter was prepared in the same way as in Example 1 using this nonwoven fabric thus polymer-coated and subjected to the blood test.

As a result, the leukocyte residual rate was $0.5\times10^{-3}$, and the filtration time was 20 minutes, demonstrating low blood process pressure and high leukocyte removal performance.

Example 10

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 55 J/g. The X-ray crystallinity was 70%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 98 dyn/cm.

A filter was prepared in the same way as in Example 1 using this nonwoven fabric thus polymer-coated and subjected to the blood test.

As a result, the leukocyte residual rate was $0.2\times10^{-3}$, and the filtration time was 18 minutes, demonstrating low blood process pressure and high leukocyte removal performance.

Example 11

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 4.7 J/g, and a quantity of heat of crystal melting of 47 J/g. The X-ray crystallinity was 59%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 98 dyn/cm.

A filter was prepared in the same way as in Example 1 using this nonwoven fabric thus polymer-coated and subjected to the blood test.

As a result, the leukocyte residual rate was $4.3\times10^{-3}$, and the filtration time was 19 minutes, demonstrating low blood process pressure and high leukocyte removal performance.

Example 12

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 4.8 J/g, and a quantity of heat of crystal melting of 53 J/g. The X-ray crystallinity was 69%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 98 dyn/cm.

A filter was prepared in the same way as in Example 1 using this nonwoven fabric thus polymer-coated and subjected to the blood test.

As a result, the leukocyte residual rate was $3.7\times10^{-3}$, and the filtration time was 17 minutes, demonstrating low blood process pressure and high leukocyte removal performance.

Example 13

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 55 J/g. The X-ray crystallinity was 58%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $2.5\times10^{-3}$, and the filtration time was 29 minutes, demonstrating low blood process pressure and high leukocyte removal performance.

Example 14

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 0.1 J/g, and a quantity of heat of crystal melting of 55 J/g. The X-ray crystallinity was 70%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $2.1\times10^{-3}$, and the filtration time was 28 minutes, demonstrating low blood process pressure and high leukocyte removal performance.

Example 15

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 4.7 J/g, and a quantity of heat of crystal melting of 47 J/g. The X-ray crystallinity was 59%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $7.3\times10^{-3}$, and the filtration time was 28 minutes, demonstrating low blood process pressure and high leukocyte removal performance.

Example 16

The nonwoven fabric used was made of PBT fibers and had a basis weight of 22 $g/m^2$, a thickness of 0.13 mm, a filling rate of 0.12, an average fiber diameter of 1.0 μm, a quantity of crystallization heat of the uncrystallized portion of 4.8 J/g, and a quantity of heat of crystal melting of 53 J/g. The X-ray crystallinity was 69%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $6.7\times10^{-3}$, and the filtration time was 28 minutes, demonstrating low blood process pressure and high leukocyte removal performance.

Example 17

The nonwoven fabric used was made of PET fibers and had a basis weight of 22 $g/m^2$, a thickness of 0.13 mm, a filling rate of 0.12, an average fiber diameter of 1.1 μm, a quantity of crystallization heat of the uncrystallized portion of 0.1 J/g, and a quantity of heat of crystal melting of 43 J/g. The X-ray crystallinity was 54%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 100 dyn/cm.

A filter was prepared in the same way as in Example 1 using this nonwoven fabric and subjected to the blood test.

During the filter preparation, ultrasonic welding was difficult to conduct, and assemblability was poor. This is probably because the nonwoven fabric had a low heat shrinkage rate and elongation rate.

As a result, the leukocyte residual rate was $0.2\times10^{-3}$, and the filtration time was 17 minutes, demonstrating low blood process pressure and high leukocyte removal performance.

Example 18

The nonwoven fabric used was made of PET fibers and had a basis weight of 22 $g/m^2$, a thickness of 0.13 mm, a filling rate of 0.12, an average fiber diameter of 1.15 μm, a quantity of crystallization heat of the uncrystallized portion of 0.1 J/g, and a quantity of heat of crystal melting of 55 J/g. The X-ray crystallinity was 71%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $3.0\times10^{-3}$, and the filtration time was 22 minutes, demonstrating low blood process pressure and high leukocyte removal performance.

Comparative Example 1

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 5.3 J/g, and a quantity of heat of crystal melting of 45 J/g. The X-ray crystallinity was 51%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 100 dyn/cm.

A filter was prepared in the same way as in Example 1 using this nonwoven fabric thus polymer-coated and subjected to the blood test.

As a result, the leukocyte residual rate was $12.5\times10^{-3}$, and the filtration time was 20 minutes, demonstrating that this filter material was practically unsuitable due to low leukocyte removal performance, though its filtration time was short.

Comparative Example 2

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 5.4 J/g, and a quantity of heat of crystal melting of 55 J/g. The X-ray crystallinity was 62%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 100 dyn/cm.

A filter was prepared in the same way as in Example 1 using this nonwoven fabric thus polymer-coated as a leukocyte removal filter material and subjected to the blood test.

As a result, the leukocyte residual rate was $10.8\times10^{-3}$, and the filtration time was 21 minutes, demonstrating that this filter material was practically unsuitable due to low leukocyte removal performance, though its filtration time was short.

Comparative Example 3

The nonwoven fabric used was made of PET fibers and had a basis weight of 22 $g/m^2$, a thickness of 0.13 mm, a filling rate of 0.12, an average fiber diameter of 1.0 μm, a quantity of crystallization heat of the uncrystallized portion of 5.3 J/g, and a quantity of heat of crystal melting of 45 J/g. The X-ray crystallinity was 51%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result, the leukocyte residual rate was $16.5\times10^{-3}$, and the filtration time was 29 minutes, demonstrating that this filter material was practically unsuitable due to low leukocyte removal performance, though its filtration time was short.

Comparative Example 4

The nonwoven fabric used was made of PET fibers and had a basis weight of 22 g/m$^2$, a thickness of 0.13 mm, a filling rate of 0.12, an average fiber diameter of 1.0 μm, a quantity of crystallization heat of the uncrystallized portion of 5.4 J/g, and a quantity of heat of crystal melting of 55 J/g. The X-ray crystallinity was 62%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result of conducting the blood test, the leukocyte residual rate was 15.4×10$^{-3}$, and the filtration time was 30 minutes, demonstrating that this filter material was practically unsuitable due to low leukocyte removal performance, though its filtration time was acceptable.

Comparative Example 5

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 5.3 J/g, and a quantity of heat of crystal melting of 45 J/g. The X-ray crystallinity was 52%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 98 dyn/cm.

A filter was prepared in the same way as in Example 1 using this nonwoven fabric thus polymer-coated and subjected to the blood test.

As a result, the leukocyte residual rate was 11.5×10$^{-3}$, and the filtration time was 20 minutes, demonstrating that this filter material was practically unsuitable due to low leukocyte removal performance, though its filtration time was short.

Comparative Example 6

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 5.4 J/g, and a quantity of heat of crystal melting of 55 J/g. The X-ray crystallinity was 63%.

The nonwoven fabric was prepared by the method involving the dry heat treatment of a fiber assembly after spinning in the same way as in Example 1. Polymer coating treatment was performed in the same way as in Example 1. The CWST value after the polymer coating treatment was 98 dyn/cm.

A filter was prepared in the same way as in Example 1 using this nonwoven fabric thus polymer-coated as a leukocyte removal filter material and subjected to the blood test.

As a result, the leukocyte residual rate was 10.1×10$^{-3}$, and the filtration time was 21 minutes, demonstrating that this filter material was practically unsuitable due to low leukocyte removal performance, though its filtration time was short.

Comparative Example 7

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 5.3 J/g, and a quantity of heat of crystal melting of 45 J/g. The X-ray crystallinity was 52%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result of conducting the blood test, the leukocyte residual rate was 14.5×10$^{-3}$, and the filtration time was 40 minutes, demonstrating that this filter material was practically unsuitable due to low leukocyte removal performance and a long filtration time.

Comparative Example 8

The nonwoven fabric used was made of PBT fibers and had a basis weight of 22 g/m$^2$, a thickness of 0.13 mm, a filling rate of 0.12, an average fiber diameter of 1.0 μm, a quantity of crystallization heat of the uncrystallized portion of 5.4 J/g, and a quantity of heat of crystal melting of 55 J/g. The X-ray crystallinity was 63%.

The nonwoven fabric was prepared by the method involving the dry heat treatment of a fiber assembly after spinning in the same way as in Example 1. The nonwoven fabric was not subjected to polymer coating treatment.

A filter was prepared in the same way as in Example 1 using this nonwoven fabric and subjected to the blood test.

As a result of conducting the blood test, the leukocyte residual rate was 13.4×10$^{-3}$, and the filtration time was 39 minutes, demonstrating that this filter material was practically unsuitable due to low leukocyte removal performance and a long filtration time.

The blood evaluation results of Examples 1 to 16 and Comparative Examples 1 to 8, the longitudinal and transverse elongation rates of the filter elements, and the specific surface areas of the nonwoven fabrics are summarized in Tables 1 to 3.

TABLE 1

| | Example 1 | Example 2 | Example 3 | Example 4 | Example 17 | Example 5 | Example 6 | Example 7 | Example 8 | Example 18 |
|---|---|---|---|---|---|---|---|---|---|---|
| Nonwoven fabric filter material | PET | PET | PET | PET | PET | PET | PET | PET | PET | PET |
| Basis weight (g/m$^2$) | 22 | 22 | 22 | 22 | 22 | 22 | 22 | 22 | 22 | 22 |
| Thickness (mm) | 0.13 | 0.13 | 0.13 | 0.13 | 0.13 | 0.13 | 0.13 | 0.13 | 0.13 | 0.13 |
| Filling rate | 0.12 | 0.12 | 0.12 | 0.12 | 0.12 | 0.12 | 0.12 | 0.12 | 0.12 | 0.12 |

TABLE 1-continued

| | | Example 1 | Example 2 | Example 3 | Example 4 | Example 17 | Example 5 | Example 6 | Example 7 | Example 8 | Example 18 |
|---|---|---|---|---|---|---|---|---|---|---|---|
| Quantity of crystallization heat of uncrystallized portion (J/g) | | 0.1 | 0.1 | 4.7 | 4.8 | 0.1 | 0.1 | 0.1 | 4.7 | 4.8 | 0.1 |
| Quantity of heat of crystal melting (J/g) | | 45 | 55 | 47 | 56 | 43 | 45 | 55 | 47 | 56 | 55 |
| X-ray crystallinity (%) | | 57 | 69 | 58 | 68 | 54 | 57 | 69 | 58 | 68 | 71 |
| Presence or absence of coating treatment | | Present | Present | Present | Present | Present | Absent | Absent | Absent | Absent | Absent |
| Raw fabric | Heat shrinkage rate (%) | 15 | 15 | 21 | 21 | 2 | 15 | 15 | 21 | 23 | 23 |
| Before sterilization | Fiber diameter (μm) | 1.0 | 1.0 | 1.0 | 1.0 | 1.1 | 1.0 | 1.0 | 1.0 | 1.15 | 1.15 |
| Before sterilization | Specific surface area ($m^2/g$) | 1.349 | 1.351 | 1.286 | 1.285 | 1.358 | 1.349 | 1.351 | 1.286 | 1.279 | 1.279 |
| Before sterilization | Elongation rate (longitudinal) (%) | 1.65 | 1.67 | 1.72 | 1.71 | 0.20 | 1.65 | 1.67 | 1.72 | 1.75 | 1.75 |
| Before sterilization | Elongation rate (transverse) (%) | 1.87 | 1.86 | 1.95 | 1.99 | 0.15 | 1.87 | 1.86 | 1.95 | 2.31 | 2.31 |
| Leukocyte residual rate ($\times 10^{-3}$) | | 0.7 | 0.3 | 5.3 | 4.3 | 0.2* | 3.3 | 2.8 | 8.3 | 7.3 | 3.0 |
| Filtration time (min) | | 20 | 18 | 19 | 17 | 17* | 23 | 21 | 22 | 18 | 22 |

*Example 17 had favorable leukocyte removal performance and filtration time, but poor filter assemblability. Thus, a higher heat shrinkage rate and elongation rates are desired for practical use.

TABLE 2

| | | Example 9 | Example 10 | Example 11 | Example 12 | Example 13 | Example 14 | Example 15 | Example 16 |
|---|---|---|---|---|---|---|---|---|---|
| Nonwoven fabric filter material | | PBT | PBT | PBT | PBT | PBT | PBT | PBT | PBT |
| Basis weight ($g/m^2$) | | 22 | 22 | 22 | 22 | 22 | 22 | 22 | 22 |
| Thickness (mm) | | 0.13 | 0.13 | 0.13 | 0.13 | 0.13 | 0.13 | 0.13 | 0.13 |
| Filling rate | | 0.12 | 0.12 | 0.12 | 0.12 | 0.12 | 0.12 | 0.12 | 0.12 |
| Quantity of crystallization heat of uncrystallized portion (J/g) | | 0.1 | 0.1 | 4.7 | 4.8 | 0.1 | 0.1 | 4.7 | 4.8 |
| Quantity of heat of crystal melting (J/g) | | 45 | 55 | 47 | 56 | 45 | 55 | 47 | 56 |
| X-ray crystallinity (%) | | 58 | 70 | 59 | 69 | 58 | 70 | 59 | 69 |
| Presence or absence of coating treatment | | Present | Present | Present | Present | Absent | Absent | Absent | Absent |
| Raw fabric | Heat shrinkage rate (%) | 14 | 14 | 22 | 22 | 14 | 14 | 22 | 22 |
| Before sterilization | Fiber diameter (μm) | 1.0 | 1.0 | 1.0 | 1.0 | 1.0 | 1.0 | 1.0 | 1.0 |
| Before sterilization | Specific surface area ($m^2/g$) | 1.355 | 1.353 | 1.287 | 1.289 | 1.355 | 1.353 | 1.287 | 1.289 |
| Before sterilization | Elongation rate (longitudinal) (%) | 1.65 | 1.67 | 1.73 | 1.72 | 1.65 | 1.67 | 1.73 | 1.72 |
| Before sterilization | Elongation rate (transverse) (%) | 2.12 | 1.98 | 2.01 | 1.95 | 2.12 | 1.98 | 2.01 | 1.95 |
| Leukocyte residual rate ($\times 10^{-3}$) | | 0.5 | 0.2 | 4.3 | 3.7 | 2.5 | 2.1 | 7.3 | 6.7 |
| Filtration time (min) | | 20 | 18 | 19 | 17 | 29 | 28 | 28 | 28 |

TABLE 3

| | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| Nonwoven fabric filter material | PET | PET | PET | PET | PBT | PBT | PBT | PBT |
| Basis weight ($g/m^2$) | 22 | 22 | 22 | 22 | 22 | 22 | 22 | 22 |
| Thickness (mm) | 0.13 | 0.13 | 0.13 | 0.13 | 0.13 | 0.13 | 0.13 | 0.13 |
| Filling rate | 0.12 | 0.12 | 0.12 | 0.12 | 0.12 | 0.12 | 0.12 | 0.12 |
| Quantity of crystallization heat of uncrystallized portion (J/g) | 5.3 | 5.4 | 5.3 | 5.4 | 5.3 | 5.4 | 5.3 | 5.4 |
| Quantity of heat of crystal melting (J/g) | 45 | 56 | 45 | 56 | 45 | 56 | 45 | 56 |

TABLE 3-continued

| | | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| X-ray crystallinity (%) | | 51 | 62 | 51 | 62 | 52 | 63 | 52 | 63 |
| Presence or absence of coating treatment | | Present | Present | Absent | Absent | Present | Present | Absent | Absent |
| Raw fabric | Heat shrinkage rate (%) | 15 | 15 | 15 | 15 | 14 | 14 | 14 | 14 |
| Before sterilization | Fiber diameter (μm) | 1.0 | 1.0 | 1.0 | 1.0 | 1.0 | 1.0 | 1.0 | 1.0 |
| Before sterilization | Specific surface area ($m^2/g$) | 1.354 | 1.356 | 1.354 | 1.356 | 1.355 | 1.353 | 1.355 | 1.353 |
| Before sterilization | Elongation rate (longitudinal) (%) | 1.64 | 1.65 | 1.64 | 1.65 | 1.67 | 1.65 | 1.67 | 1.65 |
| Before sterilization | Elongation rate (transverse) (%) | 1.91 | 1.88 | 1.91 | 1.88 | 2.00 | 1.85 | 2.00 | 1.85 |
| Leukocyte residual rate ($\times 10^{-3}$) | | 12.5 | 10.8 | 16.5 | 15.4 | 11.5 | 10.1 | 14.5 | 13.4 |
| Filtration time (min) | | 20 | 21 | 29 | 30 | 20 | 21 | 40 | 39 |

As shown in Tables 1 to 3, it was able to be confirmed from the results of Examples 1 to 18 and Comparative Examples 1 to 8 that leukocyte removal performance and a short filtration time, i.e., favorable flowability, can be achieved by producing a leukocyte removal filter using a nonwoven fabric whose quantity of crystallization heat of the uncrystallized portion is 5 J/g or smaller. It was able to be further confirmed that the leukocyte removal performance can be further improved by setting the quantity of heat of crystal melting and X-ray crystallinity of the nonwoven fabric to be high. In addition, the polymer coating treatment of the nonwoven fabric was confirmed to achieve further improvement in leukocyte removal performance and shortening of the filtration time. Thus, the providing the coat layer was confirmed to contribute to improvement in performance balance.

When PET and PBT were compared as a material for the nonwoven fabric, the PBT nonwoven fabric significantly extended the filtration time in the absence of coating treatment as compared with in the presence of coating treatment, whereas the influence of the presence or absence of coating treatment on the filtration time was found to be smaller in the PET nonwoven fabric than in PBT. This suggests that the PET nonwoven fabric permits filter design without coating treatment and is effective for reducing production cost, when the leukocyte removal performance can sufficiently satisfy the standard (Examples 5 and 6).

<Case where Filter Element was Constituted by Plurality of Nonwoven Fabrics of Different Types>

(Preparation of Blood Processing Filter)

1. Examples 21 to 25 and 31 to 35 and Comparative Examples 25 to 27

The nonwoven fabrics used were nonwoven fabric P (which was made of polyester having an average fiber diameter of 12 μm and had a basis weight of 30 $g/m^2$ and a specific surface area of 0.24 $m^2/g$), nonwoven fabric A (which was made of polyester having an average fiber diameter of 1.8 μm, subjected to coating treatment, and had a basis weight of 60 $g/m^2$ and a specific surface area of 1.1 $m^2/g$), and nonwoven fabric B (which was a polyester (PET or PBT) nonwoven fabric prepared in each of Examples and Comparative Examples, subjected to coating treatment, and had a basis weight of 40 $g/m^2$).

For the coating treatment for the nonwoven fabrics A and B, a copolymer consisting of 97% by mol of 2-hydroxyethyl (meth)acrylate and 3% by mol of dimethylaminoethyl (meth)acrylate was employed.

A laminate having a symmetric structure where the nonwoven fabrics P, A, and B were stacked in the order of P-A-B-A-P from the upstream side was prepared and used as a filter element.

This filter element was sandwiched between flexible vinyl chloride resin sheets having a port serving as an inlet or an outlet, and the peripheral portions of the filter element and the flexible sheets were integrally welded using a high-frequency welding machine to prepare a blood processing filter having an effective filtration area of 43 $cm^2$.

All of the blood processing filters were subjected to high-pressure steam sterilization treatment (steam heat treatment) at 115° C. for 60 minutes and then vacuum-dried at 40° C. for 15 hours or longer to prepare high-pressure steam-sterilized filters.

2. Examples 26 and 36 and Comparative Examples 22 to 24

The nonwoven fabrics used were nonwoven fabric P (which was made of polyester having an average fiber diameter of 12 μm and had a basis weight of 30 $g/m^2$ and a specific surface area of 0.24 $m^2/g$), nonwoven fabric A (which was made of polyester having an average fiber diameter of 1.8 μm, subjected to coating treatment, and had a basis weight of 60 $g/m^2$ and a specific surface area of 1.1 $m^2/g$), and nonwoven fabric B (which was a polyester (PET or PBT) nonwoven fabric prepared in each of Examples and Comparative Examples, subjected to coating treatment, and had a basis weight of 40 $g/m^2$).

For the coating treatment for the nonwoven fabrics A and B, a copolymer consisting of 97% by mol of 2-hydroxyethyl (meth)acrylate and 3% by mol of dimethylaminoethyl (meth)acrylate was employed.

A laminate having a symmetric structure where the nonwoven fabrics P, A, and B were stacked in the order of P-A-B from the upstream side was prepared and used as a filter element.

This filter element was filled in a polycarbonate container having a port serving as a blood inlet or outlet such that the periphery of the filter element was held by a continuous convex portion disposed in the internal side of the rigid container. The peripheral portions of the filter element and the container were integrally welded using an ultrasonic welding machine to prepare a blood processing filter having an effective filtration area of 43 $cm^2$.

All of the filters were subjected to high-pressure steam sterilization (steam heat treatment) at 115° C. for 60 minutes.

Example 21

A blood processing filter was prepared by the procedures mentioned above using nonwoven fabric B that was made of PET fibers and had a heat shrinkage rate of 5%, an average fiber diameter of 1.1 μm, a specific surface area of 1.366 $m^2/g$, a longitudinal elongation rate of 1.63%, and a transverse elongation rate of 2.24%. As a result of conducting the leukocyte removal performance test, the leukocyte removal performance before and after high-pressure steam sterilization was as shown in Table 4. Reduction in performance caused by the sterilization was not found.

Example 22

A blood processing filter was prepared by the procedures mentioned above using nonwoven fabric B that was made of PET fibers and had a heat shrinkage rate of 10%, an average fiber diameter of 1.1 μm, a specific surface area of 1.357 $m^2/g$, a longitudinal elongation rate of 1.64%, and a transverse elongation rate of 2.05%. As a result of conducting the leukocyte removal performance test, the leukocyte removal performance before and after high-pressure steam sterilization was as shown in Table 4. Reduction in performance caused by the sterilization was not found.

Example 23

A blood processing filter was prepared by the procedures mentioned above using nonwoven fabric B that was made of PET fibers and had a heat shrinkage rate of 15%, an average fiber diameter of 1.1 μm, a specific surface area of 1.352 $m^2/g$, a longitudinal elongation rate of 1.66%, and a transverse elongation rate of 1.87%. As a result of conducting the leukocyte removal performance test, the leukocyte removal performance before and after high-pressure steam sterilization was as shown in Table 4. Reduction in performance caused by the sterilization was not found.

Example 24

A blood processing filter was prepared by the procedures mentioned above using nonwoven fabric B that was made of PET fibers and had a heat shrinkage rate of 21%, an average fiber diameter of 1.2 μm, a specific surface area of 1.289 $m^2/g$, a longitudinal elongation rate of 1.71%, and a transverse elongation rate of 1.91%. As a result of conducting the leukocyte removal performance test, the leukocyte removal performance before and after high-pressure steam sterilization was as shown in Table 4. Reduction in performance caused by the sterilization was not found.

Example 25

A blood processing filter was prepared by the procedures mentioned above using nonwoven fabric B that was made of PET fibers and had a heat shrinkage rate of 24%, an average fiber diameter of 1.2 μrn, a specific surface area of 1.275 $m^2/g$, a longitudinal elongation rate of 1.75%, and a transverse elongation rate of 2.52%. As a result of conducting the leukocyte removal performance test, the leukocyte removal performance before and after high-pressure steam sterilization was as shown in Table 4. Reduction in performance caused by the sterilization was not found.

Example 26

A blood processing filter was prepared by the procedures mentioned above using nonwoven fabric B that was made of PET fibers and had a heat shrinkage rate of 15%, an average fiber diameter of 1.2 μm, a specific surface area of 1.352 $m^2/g$, a longitudinal elongation rate of 1.66%, and a transverse elongation rate of 1.87%. As a result of conducting the leukocyte removal performance test, the leukocyte removal performance before and after high-pressure steam sterilization was as shown in Table 4. Reduction in performance caused by the sterilization was not found.

Example 31

A blood processing filter was prepared by the procedures mentioned above using nonwoven fabric B that was made of PBT fibers and had a heat shrinkage rate of 5%, an average fiber diameter of 1.1 μm, a specific surface area of 1.360 $m^2/g$, a longitudinal elongation rate of 1.62%, and a transverse elongation rate of 2.17%. As a result of conducting the leukocyte removal performance test, the leukocyte removal performance before and after high-pressure steam sterilization was as shown in Table 5. Reduction in performance caused by the sterilization was not found.

Example 32

A blood processing filter was prepared by the procedures mentioned above using nonwoven fabric B that was made of PBT fibers and had a heat shrinkage rate of 10%, an average fiber diameter of 1.1 μm, a specific surface area of 1.358 $m^2/g$, a longitudinal elongation rate of 1.66%, and a transverse elongation rate of 2.42%. As a result of conducting the leukocyte removal performance test, the leukocyte removal performance before and after high-pressure steam sterilization was as shown in Table 5. Reduction in performance caused by the sterilization was not found.

Example 33

A blood processing filter was prepared by the procedures mentioned above using nonwoven fabric B that was made of PBT fibers and had a heat shrinkage rate of 15%, an average fiber diameter of 1.1 μm, a specific surface area of 1.351 $m^2/g$, a longitudinal elongation rate of 1.69%, and a transverse elongation rate of 1.88%. As a result of conducting the leukocyte removal performance test, the leukocyte removal performance before and after high-pressure steam sterilization was as shown in Table 5. Reduction in performance caused by the sterilization was not found.

Example 34

A blood processing filter was prepared by the procedures mentioned above using nonwoven fabric B that was made of PBT fibers and had a heat shrinkage rate of 21%, an average fiber diameter of 1.2 μm, a specific surface area of 1.287 $m^2/g$, a longitudinal elongation rate of 1.73%, and a transverse elongation rate of 2.25%. As a result of conducting the leukocyte removal performance test, the leukocyte removal performance before and after high-pressure steam sterilization was as shown in Table 5. Reduction in performance caused by the sterilization was not found.

Example 35

A blood processing filter was prepared by the procedures mentioned above using nonwoven fabric B that was made of PBT fibers and had a heat shrinkage rate of 24%, an average fiber diameter of 1.2 μm, a specific surface area of 1.275 $m^2/g$, a longitudinal elongation rate of 1.67%, and a transverse elongation rate of 2.33%. As a result of conducting the leukocyte removal performance test, the leukocyte removal performance before and after high-pressure steam sterilization was as shown in Table 5. Reduction in performance caused by the sterilization was not found.

Example 36

A blood processing filter was prepared by the procedures mentioned above using nonwoven fabric B that was made of PBT fibers and had a heat shrinkage rate of 14%, an average fiber diameter of 1.1 μm for the nonwoven fabric, a specific surface area of 1.355 $m^2/g$, a longitudinal elongation rate of 1.69%, and a transverse elongation rate of 1.90%. As a result of conducting the leukocyte removal performance test, the leukocyte removal performance before and after high-pressure steam sterilization was as shown in Table 5. Reduction in performance caused by the sterilization was not found.

Comparative Example 22

A blood processing filter was prepared by the procedures mentioned above using nonwoven fabric B having a heat shrinkage rate of 25%, an average fiber diameter of 1.2 μm, a specific surface area of 1.268 $m^2/g$, a longitudinal elongation rate of 1.65%, and a transverse elongation rate of 3.87%. As a result of conducting the leukocyte removal performance test, the leukocyte removal performance before and after high-pressure steam sterilization was as shown in Table 6. Reduction in performance caused by the sterilization was found.

Comparative Example 23

A blood processing filter was prepared by the procedures mentioned above using nonwoven fabric B having a heat shrinkage rate of 30%, an average fiber diameter of 1.2 μm, a specific surface area of 1.246 $m^2/g$, a longitudinal elongation rate of 1.72%, and a transverse elongation rate of 2.11%. As a result of conducting the leukocyte removal performance test, the leukocyte removal performance before and after high-pressure steam sterilization was as shown in Table 6. Reduction in performance caused by the sterilization was found.

Comparative Example 24

A blood processing filter was prepared by the procedures mentioned above using nonwoven fabric B having a heat shrinkage rate of 38%, an average fiber diameter of 1.3 μm, a specific surface area of 1.222 $m^2/g$, a longitudinal elongation rate of 1.67%, and a transverse elongation rate of 3.55%. As a result of conducting the leukocyte removal performance test, the leukocyte removal performance before and after high-pressure steam sterilization was as shown in Table 6. Reduction in performance caused by the sterilization was found.

Comparative Example 25

A blood processing filter was prepared by the procedures mentioned above using nonwoven fabric B having a heat shrinkage rate of 25%, an average fiber diameter of 1.2 μm, a specific surface area of 1.268 $m^2/g$, a longitudinal elongation rate of 1.65%, and a transverse elongation rate of 2.87%. As a result of conducting the leukocyte removal performance test, the leukocyte removal performance before and after high-pressure steam sterilization was as shown in Table 6. Reduction in performance caused by the sterilization was found.

Comparative Example 26

A blood processing filter was prepared by the procedures mentioned above using nonwoven fabric B having a heat shrinkage rate of 30%, an average fiber diameter of 1.2 μm, a specific surface area of 1.246 $m^2/g$, a longitudinal elongation rate of 1.72%, and a transverse elongation rate of 2.11%. As a result of conducting the leukocyte removal performance test, the leukocyte removal performance before and after high-pressure steam sterilization was as shown in Table 6. Reduction in performance caused by the sterilization was found.

Comparative Example 27

A blood processing filter was prepared by the procedures mentioned above using nonwoven fabric B having a heat shrinkage rate of 38%, an average fiber diameter of 1.3 μm, a specific surface area of 1.222 $m^2/g$, a longitudinal elongation rate of 1.67%, and a transverse elongation rate of 3.55%. As a result of conducting the leukocyte removal performance test, the leukocyte removal performance before and after high-pressure steam sterilization was as shown in Table 6. Reduction in performance caused by the sterilization was found.

The results of Examples 21 to 26 and 31 to 36 and Comparative Examples 21 to 27, and the thicknesses, filling rates, quantities of crystallization heat of the uncrystallized portions (values measured by DSC using TA-60WS system manufactured by Shimadzu Corp.), quantities of heat of crystal melting, and X-ray crystallinity of the nonwoven fabrics B respectively used therein are shown in Tables 4 to 6.

TABLE 4

| | Example 21 | Example 22 | Example 23 | Example 24 | Example 25 | Example 26 |
|---|---|---|---|---|---|---|
| Nonwoven fabric filter material | PET | PET | PET | PET | PET | PET |
| Basis weight ($g/m^2$) | 40 | 40 | 40 | 40 | 40 | 40 |
| Thickness (mm) | 0.19 | 0.19 | 0.19 | 0.19 | 0.19 | 0.19 |
| Filling rate | 0.15 | 0.15 | 0.15 | 0.15 | 0.15 | 0.15 |

TABLE 4-continued

| | | Example 21 | Example 22 | Example 23 | Example 24 | Example 25 | Example 26 |
|---|---|---|---|---|---|---|---|
| Quantity of crystallization heat of uncrystallized portion (J/g) | | 0.1 | 0.1 | 0.1 | 0.1 | 0.1 | 0.1 |
| Quantity of heat of crystal melting (J/g) | | 53 | 56 | 55 | 53 | 55 | 54 |
| X-ray crystallinity (%) | | 69 | 67 | 70 | 69 | 66 | 68 |
| Presence or absence of coating treatment | | Present | Present | Present | Present | Present | Present |
| Raw fabric | Heat shrinkage rate (%) | 5 | 10 | 15 | 21 | 24 | 15 |
| Before sterilization | Fiber diameter (μm) | 1.1 | 1.1 | 1.1 | 1.2 | 1.2 | 1.2 |
| Before sterilization | Specific surface area ($m^2/g$) | 1.366 | 1.357 | 1.352 | 1.289 | 1.275 | 1.352 |
| Before sterilization | Elongation rate (longitudinal) (%) | 1.63 | 1.64 | 1.66 | 1.71 | 1.75 | 1.66 |
| Before sterilization | Elongation rate (transverse) (%) | 2.24 | 2.05 | 1.87 | 1.91 | 2.52 | 1.87 |
| Before sterilization | Leukocyte residual rate ($\times 10^{-5}$) | 1.1 | 1.4 | 1.3 | 1.5 | 1.9 | 1.6 |
| After sterilization | Leukocyte residual rate ($\times 10^{-5}$) | 1.3 | 1.5 | 1.6 | 2.1 | 3.0 | 2.1 |
| Filtration time (min) | | 38 | 38 | 37 | 36 | 36 | 33 |
| Container | | PVC | PVC | PVC | PVC | PVC | PC |

TABLE 5

| | | Example 31 | Example 32 | Example 33 | Example 34 | Example 35 | Example 36 |
|---|---|---|---|---|---|---|---|
| Nonwoven fabric filter material | | PBT | PBT | PBT | PBT | PBT | PBT |
| Basis weight ($g/m^2$) | | 40 | 40 | 40 | 40 | 40 | 40 |
| Thickness (mm) | | 0.19 | 0.19 | 0.19 | 0.19 | 0.19 | 0.19 |
| Filling rate | | 0.15 | 0.15 | 0.15 | 0.15 | 0.15 | 0.15 |
| Quantity of crystallization heat of uncrystallized portion (J/g) | | 0.1 | 0.1 | 0.1 | 0.1 | 0.1 | 0.1 |
| Quantity of heat of crystal melting (J/g) | | 53 | 57 | 53 | 54 | 55 | 58 |
| X-ray crystallinity (%) | | 66 | 69 | 70 | 68 | 66 | 69 |
| Presence or absence of coating treatment | | Present | Present | Present | Present | Present | Present |
| Raw fabric | Heat shrinkage rate (%) | 5 | 10 | 15 | 21 | 24 | 14 |
| Before sterilization | Fiber diameter (μm) | 1.1 | 1.1 | 1.1 | 1.2 | 1.2 | 1.1 |
| Before sterilization | Specific surface area ($m^2/g$) | 1.360 | 1.358 | 1.351 | 1.287 | 1.275 | 1.355 |
| Before sterilization | Elongation rate (longitudinal) (%) | 1.62 | 1.66 | 1.69 | 1.73 | 1.67 | 1.69 |
| Before sterilization | Elongation rate (transverse) (%) | 2.17 | 2.42 | 1.88 | 2.25 | 2.33 | 1.90 |
| Before sterilization | Leukocyte residual rate ($\times 10^{-5}$) | 1.0 | 1.3 | 1.3 | 2.0 | 2.0 | 1.4 |
| After sterilization | Leukocyte residual rate ($\times 10^{-5}$) | 1.3 | 1.5 | 1.5 | 2.8 | 3.2 | 1.9 |
| Filtration time (min) | | 38 | 38 | 38 | 37 | 36 | 34 |
| Container | | PVC | PVC | PVC | PVC | PVC | PC |

TABLE 6

| | Comparative Example 22 | Comparative Example 23 | Comparative Example 24 | Comparative Example 25 | Comparative Example 26 | Comparative Example 27 |
|---|---|---|---|---|---|---|
| Nonwoven fabric filter material | PET | PET | PET | PET | PET | PET |
| Basis weight ($g/m^2$) | 40 | 40 | 40 | 40 | 40 | 40 |

TABLE 6-continued

| | | Comparative Example 22 | Comparative Example 23 | Comparative Example 24 | Comparative Example 25 | Comparative Example 26 | Comparative Example 27 |
|---|---|---|---|---|---|---|---|
| Thickness (mm) | | 0.19 | 0.19 | 0.19 | 0.19 | 0.19 | 0.19 |
| Filling rate | | 0.15 | 0.15 | 0.15 | 0.15 | 0.15 | 0.15 |
| Quantity of crystallization heat of uncrystallized portion (J/g) | | 5.4 | 5.5 | 5.4 | 5.4 | 5.5 | 5.4 |
| Quantity of heat of crystal melting (J/g) | | 58 | 55 | 56 | 58 | 55 | 56 |
| X-ray crystallinity (%) | | 58 | 60 | 53 | 58 | 60 | 53 |
| Presence or absence of coating treatment | | Present | Present | Present | Present | Present | Present |
| Raw fabric | Heat shrinkage rate (%) | 25 | 30 | 38 | 25 | 30 | 38 |
| Before sterilization | Fiber diameter (μm) | 1.2 | 1.2 | 1.3 | 1.2 | 1.2 | 1.3 |
| Before sterilization | Specific surface area ($m^2/g$) | 1.268 | 1.246 | 1.222 | 1.268 | 1.246 | 1.222 |
| Before sterilization | Elongation rate (longitudinal) (%) | 1.65 | 1.72 | 1.67 | 1.65 | 1.72 | 1.67 |
| Before sterilization | Elongation rate (transverse) (%) | 2.87 | 2.11 | 3.55 | 2.87 | 2.11 | 3.55 |
| Before sterilization | Leukocyte residual rate ($\times 10^{-5}$) | 3.2 | 6.3 | 12.6 | 3.3 | 10.0 | 10.2 |
| Before sterilization | Leukocyte residual rate ($\times 10^{-5}$) | 15.8 | 46.7 | 102.1 | 10.2 | 37.9 | 56.1 |
| Filtration time (min) | | 20 | 32.0 | 29.7 | 25.6 | 35.3 | 32.5 |
| Container | | PC | PC | PC | PVC | PVC | PVC |

INDUSTRIAL APPLICABILITY

The filter element of the present invention can be used for removing unnecessary components (e.g., aggregates, pathogenic substances (viruses, bacteria, protozoa, infected red cells, etc.), and drugs for blood processing) contained in blood.

Particularly, the filter element of the present invention has higher leukocyte removal performance and can shorten a processing time without causing clogging, as compared with conventional methods. Therefore, the filter element of the present invention can be suitably used as a leukocyte removal filter element, particularly, for capturing leukocytes contained in blood.

In particular, a blood processing filter using the filter element of the present invention exhibits only small reduction in performance due to steam heat treatment such as high-pressure steam sterilization and as such, is preferably used for pharmaceutical, medical and general industrial purposes using steam heat treatment under severe conditions, such as the prevention of leukocyte-induced adverse reactions of blood transfusion.

The present application is based on Japanese Patent Application Nos. 2015-122448 and 2015-122449 filed in the Japan Patent Office on Jun. 17, 2015, the contents of which are incorporated herein by reference.

REFERENCE SIGNS LIST

1 . . . Container, 3 . . . First port (liquid inlet/outlet), 4 . . . Second port (liquid inlet/outlet), 5 . . . Filter element, 7 . . . Space on the first port side, 8 . . . Space on the second port side, 9 . . . Outer edge of the filter element, 10 . . . Blood processing filter.

The invention claimed is:

1. A filter element for a blood processing filter, comprising a nonwoven fabric, wherein a quantity of crystallization heat of an uncrystallized portion of the nonwoven fabric is 5 J/g or smaller, and an X-ray crystallinity of the nonwoven fabric is 54% to 71%.

2. The filter element for a blood processing filter according to claim 1, wherein a value obtained by subtracting the quantity of crystallization heat of the uncrystallized portion of the nonwoven fabric from its quantity of heat of crystal melting is 50 J/g or larger.

3. The filter element for a blood processing filter according to claim 1, wherein an X-ray crystallinity of the nonwoven fabric is 60% to 71%.

4. The filter element according to claim 1, wherein an area contraction rate of the nonwoven fabric is 10% or smaller.

5. The filter element according to claim 1, wherein the nonwoven fabric has a nonionic group and a basic nitrogen-containing functional group in a surface portion thereof.

6. The filter element for a blood processing filter according to claim 1, wherein a heat shrinkage rate of the nonwoven fabric is from 5 to 24%, and elongation rates of the nonwoven fabric both in a direction where the elongation rate is maximized and in a direction vertical thereto are 1% or more and 3% or less.

7. The filter element for a blood processing filter according to claim 6, wherein a difference between the elongation rate of the nonwoven fabric in the direction where the elongation rate is maximized and its elongation rate in the direction vertical thereto is 1% or less.

8. A blood processing filter comprising a filter element according to claim 6, an inlet-side container member, and an outlet-side container member, wherein the inlet-side container member and the outlet-side container member are each made of a resin material, the filter element is held such that the outer edges of the filter element are bound by the inlet-side container member and the outlet-side container member, and an internal space of the blood processing filter is partitioned by the filter element into inlet space and outlet space.

9. A blood processing filter comprising a filter element according to claim 6 and a container having an inlet and an outlet, wherein the container is made of a resin material, the filter element is welded to the periphery of the container, and an internal space of the blood processing filter is partitioned by the filter element into inlet space and outlet space.

10. A blood processing filter comprising a filter element according to claim 1, an inlet-side container member, and an outlet-side container member, wherein the inlet-side container member and the outlet-side container member are each made of a resin material, the filter element is held such that the outer edges of the filter element are bound by the inlet-side container member and the outlet-side container member, and an internal space of the blood processing filter is partitioned by the filter element into inlet space and outlet space.

11. The blood processing filter according to claim 10, wherein the filter element comprises a plurality of nonwoven fabrics, and the quantity of crystallization heat of the uncrystallized portion of a nonwoven fabric contacted with the inlet-side container member and/or a nonwoven fabric contacted with the outlet-side container member among the plurality of nonwoven fabrics is 5 J/g or smaller.

12. The blood processing filter according to claim 10, wherein a packing density of the filter element is 0.1 $g/cm^3$ or higher and 0.5 $g/cm^3$ or lower.

13. The blood processing filter according to claim 10, wherein the resin material is selected from the group consisting of phenol resin, acrylic resin, epoxy resin, formaldehyde resin, urea resin, silicon resin, acrylonitrile butadiene styrene (ABS) resin, nylon, and polycarbonate.

14. A blood processing filter comprising a filter element according to claim 1 and a container having an inlet and an outlet, wherein the container is made of a resin material, the filter element is welded to the periphery of the container, and an internal space of the blood processing filter is partitioned by the filter element into inlet space and outlet space.

15. The blood processing filter according to claim 14, wherein the filter element comprises a plurality of nonwoven fabrics, and the quantity of crystallization heat of the uncrystallized portion of a nonwoven fabric contacted with the inlet-side container member and/or a nonwoven fabric contacted with the outlet-side container member among the plurality of nonwoven fabrics is 5 J/g or smaller.

16. The blood processing filter according to claim 14, wherein a packing density of the filter element is 0.1 $g/cm^3$ or higher and 0.5 $g/cm^3$ or lower.

17. The blood processing filter according to claim 14, wherein the resin material is selected from the group consisting of polyvinyl chloride, polyurethane, ethylene-vinyl acetate copolymers, polyethylene, polypropylene, hydrogenation products of styrene-butadiene-styrene copolymers, styrene-isoprene-styrene copolymers or hydrogenation products thereof, and mixtures of thermoplastic elastomers with softening agents.

18. The filter element for a blood processing filter according to claim 1, wherein a specific surface area of the nonwoven fabric is 0.8 $m^2/g$ to 5.0 $m^2/g$.

19. The filter element of claim 1, wherein the filter element is unsterilized.

* * * * *